United States Patent [19]
Graham et al.

[11] Patent Number: 6,080,569
[45] Date of Patent: Jun. 27, 2000

[54] ADENOVIRUS VECTORS GENERATED FROM HELPER VIRUSES AND HELPER-DEPENDENT VECTORS

[75] Inventors: Frank L. Graham; Robin Parks; Liane Chen, all of Hamilton, Canada

[73] Assignee: Merck & Co., Inc., Rahway, N.J.

[21] Appl. No.: 08/719,217

[22] Filed: Sep. 25, 1996

Related U.S. Application Data

[63] Continuation-in-part of application No. 08/473,168, Jun. 7, 1995, Pat. No. 5,919,676, which is a continuation-in-part of application No. 08/250,885, May 31, 1994, which is a continuation-in-part of application No. 08/080,727, Jun. 24, 1993, abandoned.

[51] Int. Cl.[7] .............................. C12N 7/00; C12N 15/63; C12N 15/09; C12N 15/83
[52] U.S. Cl. ................................... 435/235.1; 435/320.1; 435/440; 435/455; 435/457
[58] Field of Search ............................ 435/172.3, 320.1, 435/135, 235.1, 440, 455, 457; 424/93.21; 530/350; 514/2, 44

[56] References Cited

U.S. PATENT DOCUMENTS

| | | | |
|---|---|---|---|
| 4,510,245 | 4/1985 | Cousens et al. | 435/172.3 |
| 4,797,368 | 1/1989 | Carter et al. | 435/320 |
| 4,920,209 | 4/1990 | Davis et al. | 435/235 |
| 4,920,211 | 4/1990 | Tibbetts et al. | 536/27 |
| 5,670,488 | 9/1997 | Gregory et al. | 514/44 |
| 5,882,877 | 3/1999 | Gregory et al. | 435/320.1 |

FOREIGN PATENT DOCUMENTS

| | | |
|---|---|---|
| WO 93/06223 | 4/1993 | WIPO . |
| WO 93/19092 | 9/1993 | WIPO . |
| WO 93/19191 | 9/1993 | WIPO . |
| WO 94/08026 | 4/1994 | WIPO . |
| WO 94/12649 | 6/1994 | WIPO . |
| WO95/27071 | 1/1995 | WIPO . |
| WO96/13597 | 1/1996 | WIPO . |

OTHER PUBLICATIONS

Anton, M., and F. L. Graham, 1995, Site–specific recombination mediated by an adenovirus vector expressing the Cre recombinase protein: a molecular switch for control of gene expression, J. Virol. 69: 4600–4606.

Araki, K., J. Araki, J. I. Miyazaki, and P. Vassali, 1995, Site–specific recombination of a transgene in fertilized eggs by transient expression of Cre recombinase. Proc. Nat'l. Acad. Sci. USA 92: 160–164.

Bett, A. J., L. Prevec, and F. L. Graham, 1993, Packaging capacity and stability of human adenovirus type 5 vectos. J. Virol. 67: 5911–5921.

Bett, A. J., W. Haddara, L. Prev, and F. L. Graham, 1994, An efficient and flexible system for construction of adenivorus vectors with insertions or deletions in early region 1 and 3. Proc. Nat'l. Acad. Sci. USA 91: 8802–8806.

(List continued on next page.)

Primary Examiner—Bruce R. Campbell
Assistant Examiner—Deborah J. R. Clark
Attorney, Agent, or Firm—Bencen & Van Dyke, P.A.; Gerald H. Bencen; Timothy H. Van Dyke

[57] ABSTRACT

The present invention provides an improved helper-dependent vector system for production of high capacity adenoviral cloning vectors. The invention makes use of the DNA size packaging constraints imposed on a pIX-defective Ad virion that prevent such virions from packaging DNA larger than approximately 35 kb. This constraint can be used to develop helper viruses that do not package their DNA. In one embodiment, the invention combines this methodology with the Cre-loxP helper-dependent system to decrease the quantity of contaminating helper virus in vector preparations. In another embodiment the invention is used for vector growth.

21 Claims, 13 Drawing Sheets

OTHER PUBLICATIONS

C. Caravokyri et al, "Constitutive Episomal Expression of Polypeptide IX (pIX) in a 293–Based Cell Line Complements the Deficiency of pIX Mutant Adenovirus Type 5", J. Of Virology, Nov. 1995, pp. 6627–6633.

Crystal, R. G., N. G. McElvaney, M. A. Rosenfeld, C. S. Chu, A. Mastrangeli, J. G. Hay, S. L. Brody, H. A. Jaffe, N. T. Eissa, and C. Danel. 1994. Administration of an adenivorus containing the human CFTR cDNA to the respiratory tract of individuals with cystic fibrosis, Nature Genetics 8: 42–51.

DiSanto, J. P., W., Mueller, D. Guy–Grand, A. Fischer, and K. Rajewsky, 1995, Lymphoid development in mice with a targeted deletion of the interleukin 2 receptor chain, Proc. Nat'l. Acad. Sci. USA 92: 377–381.

Gage, P.J., B. Sauer, M. Levin and J.C. Glorioso. 1992. A cell–free recombination system for site–specific integration of multigenic shuttle plasmids into the herpes simplex virus type 1 genome. J. Virol. 66:5509–5515.

Graham, F. L. and L. Prevec. 1991. Manipulation of adenovirus vectors. In Murray E.J. (ed.), Methods in Molecular Biology. The Humana Press Inc. Clifton, N.J. vol. 7 (Gene Transfer and Expression Protocols): 109–128.

Graham F.L. and L. Prevec. 1992. Adenovirus–based expression vectors and recombinant vaccines in: Vaccines; New Approaches in Immunological Problems., ed. Ellis, R.W. Butterworth–Heinemann, Boston, MA: 363–390.

Graham F. L., J. Smiley, W. C. Russel and R. Nairn. 1977. Characteristics of a human cell line transformed by DNA from human adenovirus type 5., J. Gen. Virol. 36: 59–72.

Graham, F. L., 1987. Growth of 293 cells in suspension culture. J. Gen. Virol. 68: 937–940.

Gu, H., J. D. Marth, P.C. Orban, H. Mossmann and K. Rajewsky. 1994. Deletion of a DNA polymerase B gene segment in T cells using cell type–specific gene targeting. Science 265: 103–106.

M. Levero et al., Defective andnondefective adenovirus vectors for expressing foreign genes in vitro and in vivo, Gene. 101 (1991) pp. 195–202.

Metzger, D., J. Clifford, H. Chiba and P. Chambon. 1995. Conditional site–specific recombination in mammalian cells using a ligand–dependent chimeric Cre protein. Proc. Nat'l. Acad. Sci. USA 92: 6991–6995.

Mittal, S.K., McDermott, M.R., Johnson, D.C., Prevec, L. and F. L. Graham. 1993. Monitoring foreign gene expression by a human adenovirus–based vector using the firefly luciferase gene as a reporter, Virus Research, 28: 67–90.

Pichel, J. G., Lasko, and H. Westphal. 1993. Timing of SV40 oncogene activation by site–specific recombination determines subsequent tumor progression during murine less development. Oncogene 8: 3333–3342.

Sauer, B. 1994. Site–specific recombination: developments and applications. Cur. Opin. Biotech. 5: 521–527.

Sauer, B. and N. Henderson. 1989. Cre–stimulated recombination of loxP–containing DNA sequences placed into the mammalian genome. Nucl. Acids Res. 17: 147–161.

Sauer, B., and N. Henderson. 1990. Targeted insertion of exogenous DNA into the eukaryotic genome by the Cre recombinase. The New Biologist 2: 441–449.

Sauer, B., M. Whealy, A. Robbins and L. Enquist. 1987. Site–specific insertion of DNA into a pseudorabies virus vector. Proc. Nat'l. Adac. Sci. USA 84: 9108–9112.

Smith A. J. H., M. A. DeSousa, B. Kwabi–Addo, A. Heppell–Parton, H. Impey, and P. Rabbits. 1995. A site–directed chromosomal translocation induced in embryonic stem cells by Cre–loxP recombination. Nature Genetics 9: 376–385.

Sternberg, N., B. Sauer, R. Hoess, and K. Abremski. 1986. Bacteriophase P1 cre gene and its regulatory region; Evidence for multiple promotors and for regulation by DNA methylation, J. Mol. Biol. 187: 197–212.

Van Deursen, J., M. Fornerod, B. Van Ress, and G. Grosveld. 1995. Cre–mediated site specific translocation between non––homologous mouse chromosomes. Proc. Nat'l. Acad. Sci. USA 92: 7376–7380.

Hanke, T., Frank L. Graham, Kenneth L. Rosenthal and David C. Johnson. 1991. Identification of an immunodomimant cytotoxic t–lymphocyte recognition site in glycoprotein B of herpes simplex virus by using recombinant adenovirus vectors and synthetic peptides. 1991. J. of Virology, 65: 1177–1186.

Quantin, B., Leslie D. Pericaudet, Shahragim Tajbakhsh and Jean–Louis Mandel. 1992. Adenovirus as an expression vector in muscle cells in vivo. Proc. Nat'l. Acad. Scie. 89: 2581–2584.

Rosenfeld, M.A. et al., 1992. In vivo transfer of the human cystic fibrosis transmembrane conductance regulator gene to the airway epithelium, Cell. 68: 143–155.

W. J. McGrory, D. S. Baulista and F. L. Graham. 1988. A simple technique for the resue of early region 1 mutations into infectious human adenovirus type 5, Virology 163: 614–617.

Wang, P., Anton, F. L. Graham and S. Bacchetti. High Frequency recombination between loxP sites in human chromosomes mediated by an adeniovorus vector expressing Cre recombinase. Submitted for publication.

Goutam Ghosh–Choudhury et al., "Human adenovirus cloning vectors based on infectious bacterial plasmids", *Gene*, 50 1986, pp. 161–171.

K.L. Berkner and P.A. Sharp, "Generation of Adenovirus by Transfection of Plasmids", *Nucleic Acids Research*, 11(17), 1983, pp. 6003–6020.

Y. Haj–Ahmad and F.L. Graham, "Development of a Helper–Independent Human Adenovirus Vector and its Use in the Transfer of the Herpes Simplex Virus Thymidine Kinase Gene", *Journal of Virology*, 57(1), 1986, pp. 267–274.

N. Jones and T. Shenk, "Isolation of Adenovirus Type 5 Host Range Deletion Mutants Defective for Transformation of Rat Embryo Cells", *Cell*, 17, 1979, pp. 683–689.

D.S. Bautista et al, "Isolation and Characterization of Insertion Mutants in E1A of Adenovirus Type 5", *Virology*, 182, 1991, pp. 578–596.

F.L. Graham, "Covalently Closed Circles of Human Adenovirus DNA are Infectious", *The EMBO Journal* 3(12), 1984, pp. 2917–2922.

M. Ruben et al, "Covalently Closed Circles of Adenovirus 5 DNA", *Nature*, 301, 1983, pp. 172–174.

P. Hearing et al, "Identification of a Repeated Sequence Element Required to Efficient Encapsidation of the Adenovirus Type 5 Chromosome", *Journal of Virology*, 61(8), 1987, pp. 2555–2558.

N.D. Stow, "The Infectivity of Adenovirus Genomes Lacking DNA Sequences from their Left–hand Termini", *Nucleic Acids Research*, 10(17), 1982, pp. 5105–5119.

Hodgson, Exp Opin Ther. Patents 5(5),459–468.

Orkin et al., Report and Recommendations . . . Gene Therapy. NIH Press. Dec. 7, 1995, p. 1–40.

Miller et al., FASEB, vol. 9, 190–199.

Marshall, Science.269, 1050–1055.

Culver et al., TIG. 10(5), 174–178.

Neuwelt et al., Behavioral and Brain Science.18, 1–9, 1995.

Wolf, Current Opinion I Neurology.3, 743–748, 1993.

Kiby et al., Trends Genet., 9, 413–421 (1993).

Yang et al., Proc. Natl. Acad. Sci. USA, 91, 4407–4411 (May 1994).

Krougliak et al., (1995), Hum. Gene Ther. 6:1575–1586, Development of Cell Lines Capable of Complementing E1, E4 and Protein IX Defective Adenovirus Type 5 Mutants.

Parks et al., (1996) Proc. Nat'l Acad. Sci. USA 93:13565–13570 A helper–dependent adenovirus vector system: Removal of helper virus by Cre–mediated excision of the third viral packaging signal.

Russ, A. P. et al., 1996. Self–Deleting Retrovirus Vectors for Gene Therapy. J of Virol., vol. 70: 8 pp. 4927–4932.

Ghosh–Choudhury et al [The EMBO J. 6(6):1733–1739], 1987.

Graham et al. [Methods in MolecularBiology, 7:109–128 (1991)].

Grable et al [J.of Virol. 66(2) (Feb. 1992)].

Kilby et al. [TIG, vol. 9 No. 12:413–421 (Dec. 1993)].

Hermanson et al [Nucleic Acids Research. 19(18) 4943–4948 (1991)].

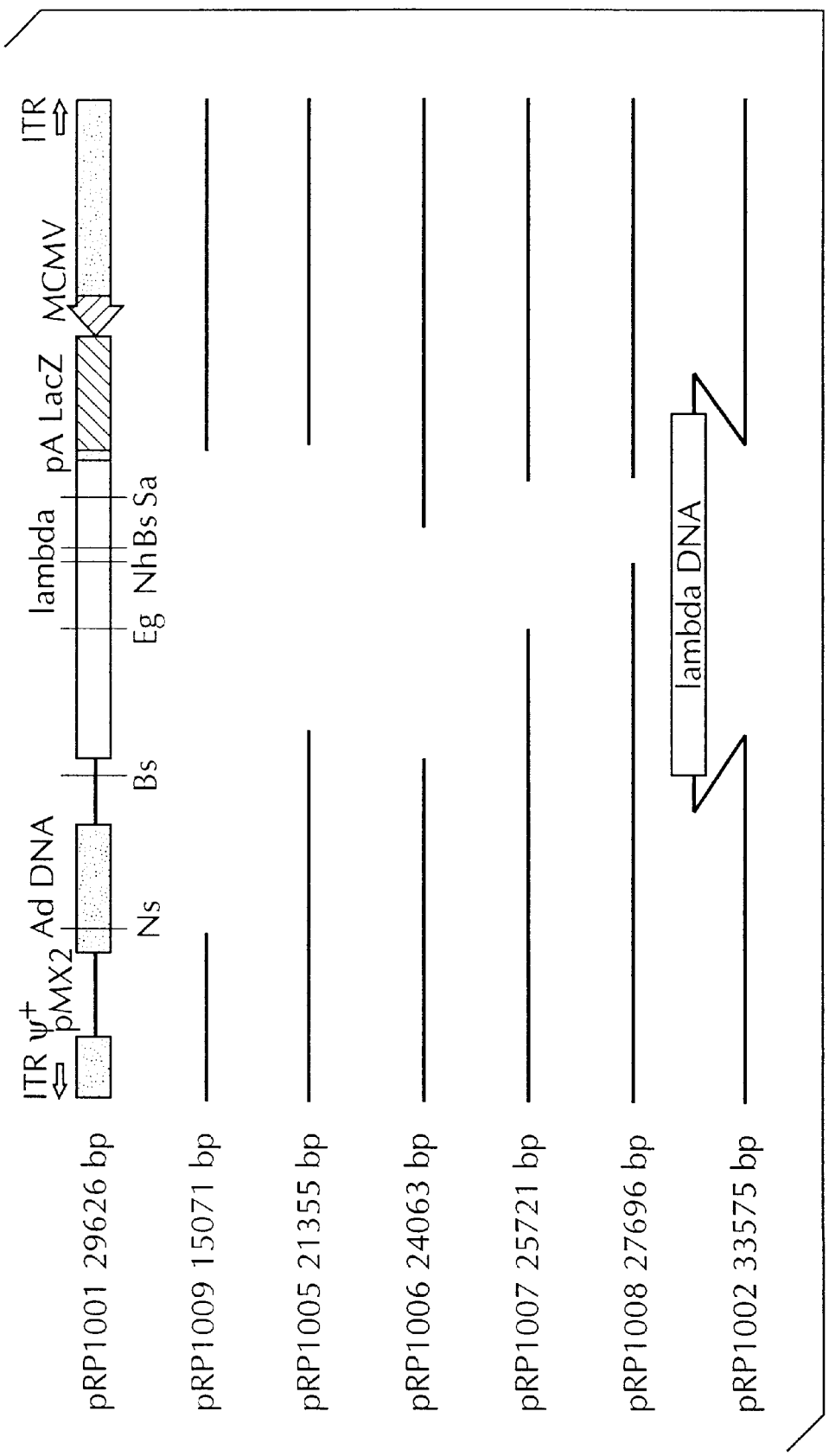

ADENOVIRUS VECTORS GENERATED FROM HELPER VIRUSES AND HELPER-DEPENDENT VECTORS

CROSS-REFERENCE TO RELATED APPLICATIONS

This application is a continuation-in-part of copending U.S. patent application Ser. No. 08/473,168 filed on Jun. 7, 1995 U.S. Pat. No. 5,919,676, Jul. 6, 1999, which is itself a copending continuation-in-part of U.S. patent application Ser. No. 08/250,885 filed on May 31, 1994, which is a continuation-in-part of abandoned U.S. patent application Ser. No. 08/080,727, filed Jun. 24, 1993 abn. from which priority is also claimed. All of these applications are hereby incorporated by reference.

FIELD OF THE INVENTION

The present invention relates to the construction of adenovirus vectors that have increased safety and stability for gene transfer in mammalian cells. The vector system described herein is an improvement and modification of the helper-dependent system, described in copending Patent No. 5,919,676.

BACKGROUND OF THE INVENTION

Adenoviruses (Ads) are a family of DNA viruses characterized by icosahedral, non-enveloped capsids containing a linear DNA genome.

The human adenovirus type 5 (Ad5) has a linear, double-stranded genome of approximately 36 kb, divided into early and late viral functions (see Berkner 1992, *Curr. Topics Micro. Immunol.* 158:39–66). A representative Adenovirus 5 ("Ad5") genome for use with the embodiments of the present invention is a 36 kB linear duplex. Its sequence has been published. (Chroboczek, J., Bieber, F., and Jacrot, B. (1992) The Sequence of the Genome of Adenovirus Type 5 and Its Comparison with the Genome of Adenovirus Type 2, *Virology* 186, 280–285; hereby incorporated by reference).

Upon infection of permissive cells, the first region transcribed from the Ad5 viral genome, E1A at the left end of the conventional map, encodes proteins that are involved in transactivation of other viral early and late genes. E1B, also at the left end of the genome, encodes proteins that regulate host cell and viral RNA and protein synthesis, and protect cells from E1A-induced apoptosis. Thus, E1 functions encoded by E1A and E1B are essential for viral replication. E1-deleted virus can be propagated in the 293 cell line which contains and expresses E1 of Ad5 (Graham et al. 1977).

Removal of the essential early regions 1A and 1B (E1A and E1B) of Ad5 generates conditional helper-independent Ads that can be grown and propagated in the E1-complementing 293 cell line (Graham et al. 1977, *J. Gen. Virol*, 36:59–72). Foreign genes have been cloned into the replication-defective Ads, and these vectors have been used extensively for the delivery of genes into mammalian cells for gene therapy, as recombinant viral vaccines, or for general purpose expression vectors for experimental studies. Ads also have the advantage that they are well characterized both genetically and biochemically, easy to manipulate, and can be grown to a very high titer. Furthermore, adenovirus is a relatively safe vector that has not been associated with any neoplastic disease, and usually causes relatively mild infections in immuno-competent individuals.

E1-deleted Ad vectors can accommodate DNA inserts of ~4.7 kb (up to 105% of the wild-type genome), and deletions in the non-essential E3 region can further increase the cloning capacity to ~8 kb (Bett et al. 1993, *J. Virol.* 67:5911–5921). However, Ad vectors with DNA inserts that increase the genome size to greater than 105% of wild-type DNA content are either non-viable or unstable, and frequently undergo DNA rearrangements to reduce the overall size of the vector (Ghosh-Choudhury et al. 1987, *EMBO J.* 6:1733–1739; Bett et al. 1993, *J. Virol.* 67:5911–5921). This is presumably due to a destabilization of the capsid because of the increased DNA content. Thus, the size of DNA inserts in "first generation" Ad vectors (i.e., E1-deleted and/or E3 deleted) is limited by the necessity to retain sufficient Ad coding sequences to allow helper-independent growth, limiting the size of "non-essential" regions that can be deleted from the genome, and the need to maintain virion stability.

Stability of the adenovirus capsid is conferred, at least in part, by protein IX (pIX). pIX has been shown to be associated with the hexons that make up the "facets" of the icosahedron (Furcinitti et al. 1989, *EMBO J.* 8:3563–3570) Although originally thought to be dispensable for virion formation (Colby and Shenk 1981, *J. Virol.* 39:977–980), pIX is required for the packaging of full-length viral DNA molecules (Haj-Ahmad and Graham 1986, *J. Virol.* 57:267–274). Deletion or inactivation of pIX results in virions that are heat labile with capsids that can accommodate only 35 kb of viral DNA (~97% of the wild-type genome). Thus, deletion or inactivation of pIX provides a means of selecting for virions that contain viral DNA that is less than the size of the wild-type genome.

Previously, the lower limit of adenovirus DNA necessary to achieve Ad DNA packaging could not be identified due to the necessity for retaining sufficient protein-coding regions to enable the production of all of the proteins required for Ad DNA replication and virion formation. The development of helper-dependent systems has alleviated this problem. In the helper-dependent systems, a helper virus provides all of the functions necessary in trans for the packaging of an helper-dependent vector, which lacks virtually all virus specific coding sequences. The helper-dependent vector contains only those cis-acting elements required for viral DNA replication and packaging. Since the sequences required for Ad DNA replication and packaging are contained within ~500 bp of the left and right ends of the genome (Grable and Hearing 1992, *J. Virol.* 66:723–731), helper-dependent vectors can, in theory, range in size from a few hundred base pairs to greater than the size of wild-type Ad, potentially carrying up to ~37 kb of foreign DNA. However, it has been demonstrated that Ad vectors that have substantially less DNA than wild-type Ads undergo DNA rearrangements and multimerization (Fisher et al. 1996, *Virol.* 217:11–22).

Despite all of the advantages of first generation Ad vectors as vectors for the delivery of foreign genes into mammalian cells, current helper-independent vectors retain many viral genes that, when expressed at low levels, may contribute to the induction in the host of an immune response against the transduced cell (Dong et al. 1996, *Hum. Gene Ther.* 7:319–33 1), resulting in the elimination of the transduced cell. The immune response will ultimately limit the usefulness of current vectors for the treatment of genetic diseases, such as cystic fibrosis, due to the requirement for long term, stable expression in order to correct the genetic deficiencies. Attempts to reduce the expression of viral genes, by the elimination of most, if not all, viral-specific coding sequences, have led to the development of the helper-dependent systems for the generation of Ad vectors (Mitani et al. 1995, *Proc. Natl. Acad. Sci.* 92:3854–3858; Fisher et al. 1996, Virol. 217:11–22; Kochanek et al. 1996, PNAS 92:5731–5736; Parks et al. 1996, *Proc. Natl. Acad. Sci.* in press). Previously, we developed a helper-dependent system that utilized a helper virus that had a packaging signal flanked by loxP sites (Parks et al. 1996, *Proc. Natl. Acad. Sci.* in press). The general principle is outlined in FIG. 1. Upon infection of a 293 cell line that constitutively expressed the Cre recombinase (293Cre; Chen and Graham, unpublished results), the packaging signal was efficiently excised from the helper virus rendering it unpackageable. However, the helper virus DNA was able to replicate and provide all of the functions necessary in trans for the packaging of a helper-dependent vector, which contained only those cis-acting elements required for viral DNA replication and packaging. Serial passage of the helper-dependent vector in helper-virus infected 293Cre cells allowed us to produce large quantities of the helper-dependent vector ($10^{10}$ transducing particles from $4\times10^8$ 293Cre cells with an initial level of contamination with helper virus of approximately 0.3–1). After fractionation on CsCl buoyant density gradients, final vector preparations contained less than 0.01 helper virus contamination, a level that is lower than in all other helper-dependent systems reported to date. The contamination of vector with helper virus that is observed is caused by helper virus DNA (~10%) that escapes the Cre-mediated excision event, and can therefore be packaged into infectious virions. At present, it is not known why these DNAs are not cleaved by Cre, but it may be due to saturation of the Cre protein in the 293Cre cells. Regardless of the reason for the helper virus contamination of vector stocks, it is apparent that modifications to the system are desired to eliminate the remaining helper virus. It is an object of the present invention to provide an improved method for preparing helper-dependent vectors. The invention herein may be used independently for vector growth or may be combined with the Cre/loxP helper-dependent system to provide a means for vector production without contaminating helper virus.

SUMMARY OF THE INVENTION

It is an object of this invention to provide a simple and useful improved helper-dependent adenovirus vector system by which high capacity adenovirus cloning vectors may be developed. The invention makes use of the DNA size packaging constraints imposed on a pIX-defective Ad virion that prevent such virions from packaging DNA larger than approximately 35 kb. This constraint can be used to develop helper adenoviruses that do not package their DNA. Additionally, one embodiment of the invention combines this methodology with the Cre-loxP helper-dependent system to decrease the quantity of helper virus in vector preparations. Such helper virus, though not able to package DNA into infectious virions, can replicate and provide all of the functions in trans for the packaging of a second vector known as the helper-dependent adenovirus vector that lacks substantial portions of the Ad coding sequences.

In accordance with the present invention, helper viruses having genomes of a size greater than the upper limit for packaging in a pIX-defective virion are provided. One embodiment of the present invention is the construction of a helper virus from two vectors. Preferably, the first vector includes a circularized, modified human adenovirus type 5 (Ad5) genome that is deleted for, or contains mutations in, the DNA sequence encoding pIX. This first vector is combined with a second vector containing overlapping viral DNA sequences to generate infectious Ad5, known as a helper virus having a modified pIX, and a genome size greater than the is upper limit for packaging in a pIX-defective virion. Alternatively, the size of the helper virus can be increased by the insertion of additional DNA sequences into the adenoviral genome, known as "stuffer" DNA. Bacterial plasmids are preferred vectors for obtaining the helper virus. However, other vectors may be employed to construct the helper virus, such as, for example, yeast plasmids.

Although not able to produce adequate proteins, particularly pIX, to permit its own packaging, the helper virus described herein, is able to produce all of the functions required for the packaging of a helper-dependent viral vector having a genome of appropriately reduced size (i.e., less than about 35 kb) and lacking substantial portions of the viral genome so that the helper-dependent vector DNA can be packaged in pIX-defective virions. Such helper virus and helper-dependent vector DNA may replicate when coinfected into appropriate host cells, but only the helper-dependent vector DNA can be packaged. Optionally, certain regions of the vectors and resulting viruses may be deleted, such as sequences in the Ad E1 or E3 regions that can be omitted from the viral genome without preventing the viral genome from replicating in such cells as may be permissive for replication of said genome in the form of infectious virus.

The vectors used to generate the helper virus and the resulting helper viruses may also contain sequences that can be recognized by a site specific recombinase. For example, Cre recombinase is suitable for use with the present invention. Recombination catalyzed by Cre acting on an appropriately constructed viral genome will result in the excision of a nucleotide sequence, known as the packaging signal($\psi$), near the left end of the viral genome, that is required for the packaging of adenoviral DNA into infectious particles. Use of the Cre recombinase in this and other examples is not meant to be limiting as other site specific recombination systems do exist and might also be employed. An example, not meant to be limiting, is the use of the yeast FLP recombinase and its recognition sequences (O'Gorman et al. 1991, *Science* 251:13–51), which could readily be substituted for the Cre protein in this and other examples.

Alternatively, vectors for generating the helper virus and the resulting helper virus having mutations in the Ad packaging signal that result in reduced efficiency of DNA packaging are suitable for use with the present invention.

A second embodiment of the present invention provides helper-dependent vectors having Ad genomes that are unable to replicate as viruses in the absence of viral products provided by a second virus, i.e., the helper virus. In one embodiment of the present invention helper-dependent vectors are derived from bacterial plasmids that contain only those viral sequences required for the replication and packaging of Ad DNA. These sequences include approximately 500 bp of viral DNA including the viral inverted terminal repeats (ITRs) and packaging signal ($\psi$), normally located at the left end of the genome. In the bacterial plasmid constructs, the left end of the left ITR is joined in a head-to-tail manner to the right ITR. Preferably, the helper-dependent viral vector also contains restriction enzyme sites suitable for the insertion of foreign DNA sequences. optionally, the bacterial plasmids used to produce the helper-dependent vectors, may contain substantial deletions of the viral DNA sequences that are substituted with large insertions of foreign DNA, for a total size of up to 35 kb in length. Such genomes are unable to replicate as viruses in the absence of viral products provided by a helper virus.

It is another object of the invention to provide helper-dependent vectors having optimum DNA packaging lengths.

In addition to possessing an upper packaging limit, the Ads of the present invention possess a lower packaging limit corresponding to approximately 75% of the wild-type genome length. Although DNAs with sizes less than this minimum are packaged, they apparently do so at a lower efficiency, resulting in a reduced virus recovery. Fisher et al. (1996) have developed a helper-dependent system utilizing a helper virus with a mutated packaging signal, and have used this system to amplify a vector of 5.5 kb. Analysis of the final viral stocks showed that the vector DNA had undergone DNA rearrangements and multimerization. This is consistent with our results showing that vectors less than ~27 kb are packaged with a lower efficiency. Vector DNA which had undergone rearrangements, resulting in a net increase in size above this lower limit would be highly selected and would likely outgrow the smaller vector.

A third embodiment of the present invention is a mammalian cell line, such as a human cell line, that provides Cre recombinase. Alternatively, Cre may be provided by another source, such as a bacterial plasmid or Ad derived vector, that expresses the Cre protein in suitable cells.

A fourth embodiment of the invention, provides a mammalian cell line, such as a human cell line that expresses the Ad pIX protein. Alternatively, pIX may be provided by another source, such as a bacterial plasmid or Ad derived vector, that expresses the pIX protein in suitable cells.

In a preferred embodiment of the present invention, a helper virus is provided that contains a deletion or mutation of pIX coding sequences and has a genome of such a size that it cannot be packaged in the absence of pIX, but can be propagated under permissive conditions, and used to support replication of a second virus, i.e., the helper-dependent vector, from which substantial portions of the viral genome have been deleted and substituted with foreign DNA having an overall DNA size that can be packaged. Under nonpermissive conditions, i.e., in the absence of pIX, the helper virus DNA described herein is unable to be packaged into infectious virions but the helper-dependent vector DNA, being smaller than ~35 kb in size, is able to be packaged into a virion capsid lacking pIX.

As previously described in copending U.S. Pat. No. 5,919,676, packaging of the helper-dependent vector of the present invention can be enhanced relative to the helper virus DNA by the Cre-mediated removal of the viral packaging signal from the helper virus DNA. However, the invention described herein provides an improved helperdependent vector system exhibiting reduced helper virus titers without the need for removal of the packaging signal from helper virus DNA as in the Cre/loxP system.

A fifth embodiment of the invention provides a kit for obtaining packaged helper-dependent vectors.

BRIEF DESCRIPTION OF THE DRAWINGS

FIG. 11 is a diagrammatic representation of helper-dependent adenovirus vector maps wherein the vectors range in size from about 15 kb to about 33 kb.

DETAILED DESCRIPTION OF THE INVENTION

The recombinant Ad vectors described herein are significantly different than other vectors currently in use which typically have deletions in E1 ("first generation" vectors) or other regions in addition to E1, such as E2 or E4 ("second generation" vectors), resulting in virus attenuation and conditional growth. The helper-dependent vector system herein uses vectors that have substantial deletions of the viral DNA coding sequences that are designed such that, in the presence of a helper adenovirus which provides all of the functions necessary for viral replication and packaging, but is itself unable to be packaged, the helper-dependent adenovirus vector is replicated and packaged into infectious virions. We have previously shown that a helper virus, rendered unpackageable by the Cre-mediated excision of a loxp flanked packaging signal (ψ), can provide all the functions necessary for the generation of an Ad vector containing the viral ITRs and packaging signal (Parks et al., Proc. Natl. Acad, Sci. in press). However, excision of the packaging signal did not occur with 100% efficiency in the 293Cre cell line, and approximately 10% of the viral DNA escaped the Cre-mediated excision event, and was packaged into virions, resulting in contamination of the vector stocks with helper virus. The invention described herein is designed to eliminate this residual helper virus and produce vector stocks free of helper virus contamination.

For viral DNA replication and packaging of viral DNA into virion particles, only three regions of the viral DNA are known to be required in cis. These are the left inverted terminal repeat, or ITR (bp 1 to approximately 103) the packaging signals (approximately 194 to 358 bp) (Hearing and Shenk, 1983, *Cell*, 33: 695–703; Grable and Hearing 1992, *J Virol.*, 64: 2047–2056) and the right ITR. All other regions of the viral genome appear to be required only to produce viral products that act in trans to allow viral replication and production of infectious viruses. Thus, if all essential viral proteins and RNA are provided by a helper virus, a helper-dependent vector can be designed and constructed that has most of the viral DNA deleted except for those sequences mentioned above that are required in cis for viral DNA replication and packaging.

In adenovirus, pIX is involved in stabilization of the virion, and pIX-defective capsids cannot package DNA greater in size than approximately 97% of the wild-type genome (~35 kb, Ghosh-Choudhury et al. 1987, *EMBO J.* 6: 1733–1739). This characteristic of adenovirus can be used to achieve selective packaging of viral DNA. For example, in a mixed population of pIX-defective viral DNA, genomes that are greater than 35 kb will not be packaged whereas those that are less than 35 kb can be packaged and will go on to form infectious virions.

Figure 1:
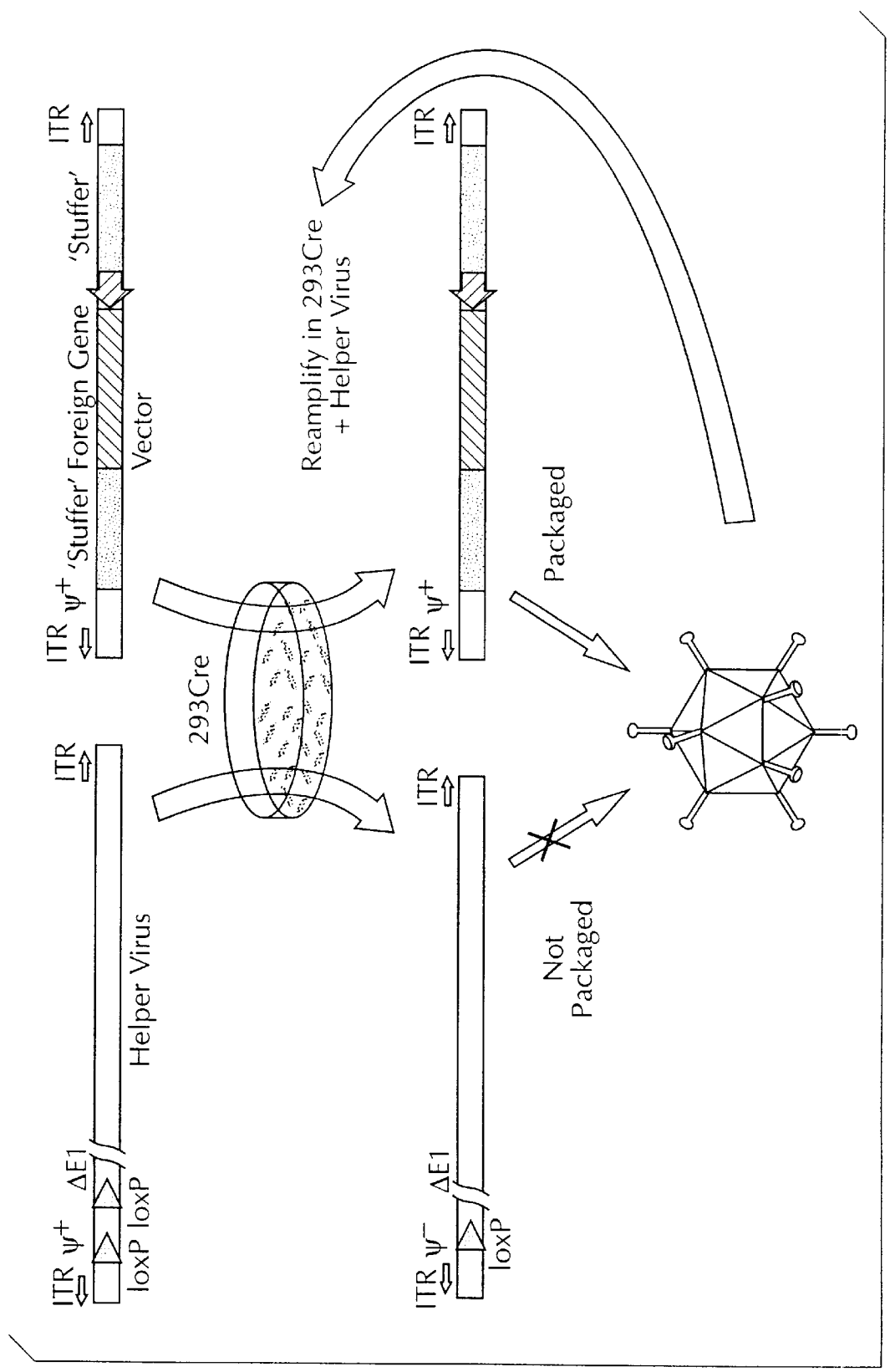
FIG. 1 is a diagrammatic representation of the Cre/loxP helper-dependent system.
Figure 2:
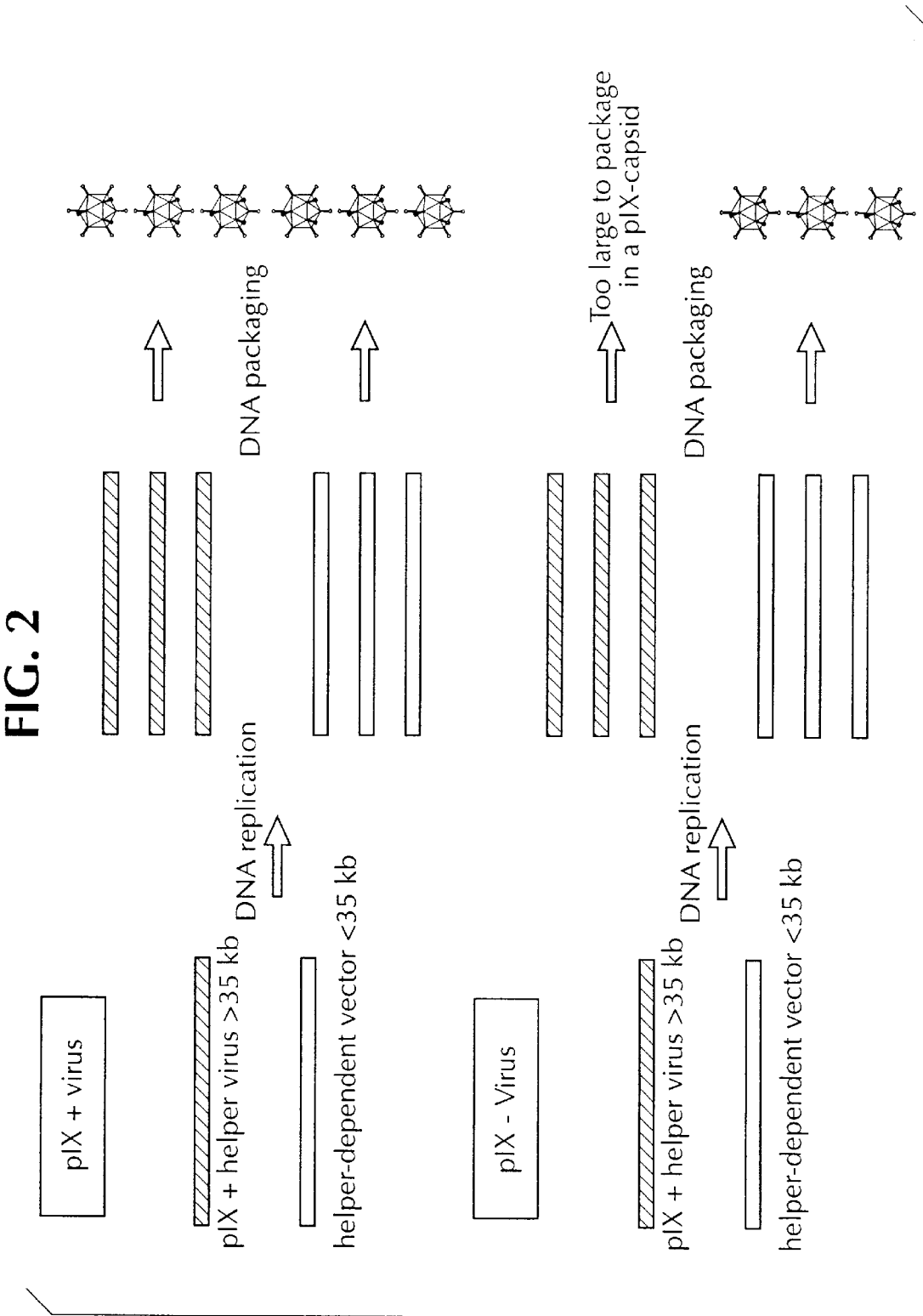
FIG. 2 is a diagrammatic representation of selective DNA packaging in the absence of pIX.

The present invention utilizes this selective packaging constraint to produce an improved helper-dependent vector system by constructing a pIX-defective helper virus such that its genome is greater than the upper limit of packaging in a pIX-defective virion, i.e., greater than about 35 kb. If pIX is provided in trans, either by use of a cell line that stably expresses the protein or by introduction of a plasmid or virus that expresses the protein, the helper virus DNA will be packaged efficiently. In the absence of pIX expression, the helper virus DNA will be replicated and all of the proteins required for virion formation will be produced (with the exception of pIX); however, the helper virus will not be packaged due to its large size. The viral functions produced by the helper virus can be used to complement the replication of a vector containing the appropriate cis-acting elements (i.e., viral packaging signal and inverted terminal repeats), providing the helper-dependent vector DNA is within the size limits allowable for a pIX-defective virion (FIG. 2). The present invention demonstrates that Ad vectors may be recovered most is efficiently when their genomes are within the 27 to 37 kb size "window". For vectors recovered using pIX-defective helper virus, the upper limit of this window will be reduced to approximately 35 kb.

Any publications referenced herein are hereby incorporated by reference in this application in order to more fully describe the state of the art to which the present invention pertains.

It is important to an understanding of the present invention to note that all technical and scientific terms used herein, unless otherwise defined, are intended to have the same meaning as commonly understood by one of ordinary skill in the art. The techniques employed herein are also those that are known to one of ordinary skill in the art, unless stated otherwise.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

The terms used herein are not intended to be limiting to the invention. For example, the term "gene" includes DNAs, cDNAs, RNAs, or other polynucleotides that encode gene products. "Foreign gene" denotes a gene that has been obtained from an organism or cell type other than the organism or cell type in which it is expressed; it also refers to a gene from the same organism that has been translocated from its normal situs in the genome.

In using the terms "nucleic acid", "RNA", "DNA", etc., we do not mean to limit the chemical structures that can be used in particular steps. For example, it is well known to those skilled in the art that RNA can generally be substituted for DNA, and as such, the use of the term "DNA" should be read to include this substitution. In addition, it is known that a variety of nucleic acid analogues and derivatives can be made and will hybridize to one another and to DNA and RNA, and the use of such analogues and derivatives is also within the scope of the present invention.

"Expression" of a gene or nucleic acid encompasses not only cellular gene expression, but also the transcription and translation of nucleic acids(s) in cloning systems and in any other context. The term "recombinase" encompasses enzymes that induce, mediate or facilitate recombination, and other nucleic acid modifying enzymes that cause, mediate or facilitate the rearrangement of a nucleic acid sequence, or the excision or insertion of a first nucleic acid sequence form or into a second nucleic acid sequence.

The "target site" of a recombinase is the nucleic acid sequence or region that is recognized (excised, cut or induced to recombine) by the recombinase.

The term "gene product" refers primarily to proteins and polypeptides encoded by a nucleic acid, but further encompasses nucleic acids encoded by other nucleic acids (e.g., non-coding and regulatory RNAs such as tRNA and sNRPs).

The term "regulation of expression" refers to events or molecules that increase or decrease the synthesis, degradation, availability or activity of a given gene product.

The present invention is also not limited to the use of the cell types and cell lines used herein. Cells from different tissues (breast, epithelium, colon, lymphocytes, etc.) or different species (human, mouse, etc.) are also suitable for use with the present invention.

It is important in this invention to detect the generation and expression of recombinant nucleic acids and their encoded gene products. The detection methods used herein include, for example, cloning and sequencing, ligation of oligonucleotides, use of the polymerase chain reaction and variations thereof (e.g., a PCR that uses 7-deaza GTP), use of single nucleotide primer-guided extension assays, hybridization techniques using target-specific oligonucleotides that can be shown to preferentially bind to complementary sequences under given stringency conditions, and sandwich hybridization methods.

Sequencing may be carried out with commercially available automated sequencers utilizing labeled primers or terminators, or using sequencing gel-based methods. Sequence analysis is also carried out by methods based on ligation of oligonucleotide sequences which anneal immediately adjacent to each other on a target DNA or RNA molecule (Wu and Wallace, *Genomics*, 4: 560–569 (1989); Landren et al., *Science*, 241: 1077–1080 (1988); Nickerson et al., *Proc. Natl. Acad. Sci.*, 88: 189–193 (1991)). Ligase-mediated covalent attachment occurs only when the oligonucleotides are correctly base-paired. The Ligase Chain Reaction (LCR), which utilizes the thermostable Taq ligase for target amplification, is particularly useful. The elevated reaction temperatures permit the ligation reaction to be conducted with high stringency (Barany, F., *PCR Methods and Applications* 1: 5–16 (1991)).

Hybridization reactions may be carried out in a filter based format, in which the target nucleic acids are immobilized on nitrocellulose or nylon membranes and probed with oligonucleotide probes. Any of the known hybridization formats may be used, including Southern blots, slot blots, "reverse" dot blots, solution hybridization, solid support based sandwich hybridization, bead-based, silicon chip based and microtiter well-based hybridization formats.

The detection oligonucleotide probes range in size between 10–1,000 bases. In order to obtain the required target discrimination using the detection oligonucleotide probes, the hybridization reactions are generally run between about 20° to about 60° C., and most preferably between about 30° to about 50° C. As known to those skilled in the art, optimal discrimination between perfect and mismatched duplexes is obtained by manipulating the temperature and/or salt concentrations or inclusion of formamide in the stringency washes.

The cloning and expression vectors described herein are introduced into cells or tissues by any one of a variety of methods known in the art. Such methods are described from example in Sambrook et al., *Molecular Cloning: A Laboratory Manual*, Cold Spring Harbor Laboratory, New York (1992), which is hereby incorporated by reference, and in Auubel et al., *Current Protocols in Molecular Biology*, John Wiley and Sons, Baltimore, MD (1989), which is also hereby incorporated by reference. The methods include, for example, stable or transient transfection, lipofection, electroporation and infection with recombinant viral vectors.

The protein products or recombined and unrecombined coding sequences may be analyzed using immune techniques. For example, a protein, or a fragment thereof is injected into a host animal along with an adjuvant so as to generate an immune response. Immunoglobulins which bind the recombinant fragment are harvested as an antiserum, and are optionally further purified by affinity chromatography or other means,. Additionally, spleen cells may be harvested from an immunized mouse host and fused to myeloma cells to produce a bank of antibody secreting hybridoma cells. The bank of hybridoma s is screened for clones that secrete immunoglobulins which bind the recombinantly produced fragment. More specifically, immunoglobulins that selectively bind to the variant polypeptides are selected either, by pre-absorption with wild-type proteins or by screening of hybridoma cell lines for specific idiotypes that bind the variant, but not wild-type polypeptides.

Nucleic acid sequences capable of ultimately expressing the desired variant polypeptides are formed from a variety of different polynucleotides (genomic or cDNA, RNA, synthetic oligonucleotides, etc.) as well as by a variety of different is techniques.

The DNA sequences are expressed in hosts after the sequences have been operably linked to (i.e., positioned to ensure the functions of) an expression control sequence. These expression vectors are typically replicable in the host organisms either as episomes or as an integral part of the host chromosomal DNA. Commonly, expression vectors contain selection markers (e.g., markers based on tetracycline resistance or hygromycin resistance) to permit detection and/or selection of those cells transformed with the desired DNA sequences. Further details can be found in U.S. Pat. No. 4,704,362.

Polynucleotides encoding a variant polypeptide include sequences that facilitate transcription (expression sequences) and translation of the coding sequences such that the encoded polypeptide product is produced. Construction of such polynucleotides is well known in the art. For example, such polynucleotides include a promoter, a transcription termination site (polyadenylation site in eukaryotic expression hosts), a ribosome binding site, and, optionally, an enhancer for use in eukaryotic expression hosts, and optionally sequences necessary for replication of a vector.

*E. coli* is one prokaryotic host useful particularly for cloning DNA sequences of the present invention. Other microbial hosts suitable for use include bacilli, such as *Bacillus subtilis*, and other enterobacteriaceae, such as Salmonella, Serratia, and various Pseudomonas species. Expression vectors are made in these prokaryotic hosts which will typically contain expression control sequences compatible with the host, such as a lactose promoter system, a beta-lactamase promoter system, or a promoter system from phage lambda. The promoters typically control expression, optionally with an operator sequence, and have ribosome binding site sequences, for example, for initiating and completing transcription and translation.

Other microbes, such as yeast, are used for expression. Saccharomyces is a suitable host, with suitable vectors having expression control sequences, such as promoters, including 3-phosphoglycerate kinase or other glycolytic enzymes, and an origin of replication, termination sequences, etc., as desired.

In addition to microorganisms, mammalian tissue cell culture is used to express and produce the polypeptides of the present invention. Eukaryotic cells are preferred, because a number of suitable host cell lines capable of secreting intact human proteins have been developed in the art, and include the CHO cell lines, various COS cell lines, HeLa cells, myeloma cell lines, Jurkat cells, and so forth. Expression vectors for these cells include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, and so forth. The vectors containing the DNA segments of interest (e.g., polypeptides encoding a variant polypeptide) are transferred into the host cell by well-known methods, which vary depending on the type of cellular host. For example, calcium chloride transfection is commonly utilized for prokaryotic cells, whereas calcium phosphate treatment or electroporation is useful for other cellular hosts.

A kit for generating the adenovirus vectors of the present invention is provided which comprises a carrier compartmentalized to receive in close confinement one or more containers wherein a first container includes helper virus in a host cell line for replicating and propagating the helper virus, a second container includes a helper-dependent vector, and a third container includes a cell line for replicating, expressing, and packaging helper-dependent adenovirus vector, and other containers include reagents and solutions necessary for carrying out the method of the present invention.

The method also lends itself readily to the formulation of test kits for use in diagnosis. Such a kit comprises a carrier compartmentalized to receive in close confinement one or more containers wherein a first container contains suitably labeled DNA probes. Other containers contain reagents useful in the localization of the labeled probes, such as enzyme substrates. Still other containers contain restriction enzymes, buffers etc., together with instructions for use.

It is also important to note that the present invention is not limited to the use of all of the described discoveries or embodiments explicitly described herein. Although combining them may indeed by preferred, it is not necessary to the invention that all aspects be used simultaneously.

The examples provided herein are illustrative of the present invention, and are not intended in any way to be limiting, as it should readily be apparent to those skilled in the art how alternative means might be used to achieve the results that this invention provides.

The helper virus described herein is designed with a defective or deleted pIX coding sequences. In one embodiment of the invention, the helper virus will also contain a loxP-flanked packaging signal, as was used in the Cre/loxP helper-dependent system in the Cre/loxP copending patent U.S. Pat. No. 5,919,676. Although not completely essential for the functioning of a pIX helper-dependent system, removal of the helper virus packaging signal, by Cre-mediated excision, will reduce competition in the infected cells for limited packaging factors, and ultimately enhance the packaging of the vector. This example is not meant to be limiting since other recombination systems are available. For example, "FLP" recombinase is an alternative recombinase suitable for use with the present invention.

Figure 3A:
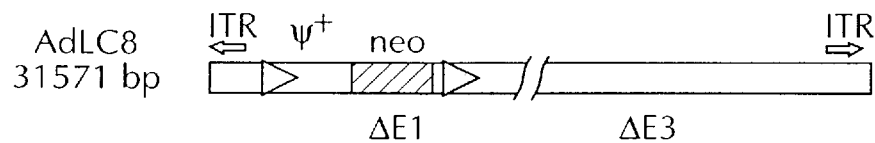
FIGS. 3(A–B) is a diagrammatic representation of the helper viruses used in the Cre/loxP and Cre/loxP/ΔpIX systems.

Alternatively, mutations of the helper-virus packaging signal can be employed to reduce the efficiency of helper virus DNA packaging. A comparison of the helper virus used in the Cre/loxP system, as outlined in the Cre/loxP helper-dependent system patent U.S. Pat. No. 5,919,676, and the helper virus in the present invention are shown in FIG. 3. The helper virus used previously, AdLC8, contains two loxP sites in a parallel orientation flanking the viral packaging signal, a neomycin (neo) resistance gene and deletions of the E1 and E3 regions (FIG. 3A). AdLC8 can replicate in cells such as 293 cells that are normally permissive for growth of an E1-deleted Ad. However, upon infection of cells that express the Cre recombinase, the packaging signal is excised rendering the viral DNA unpackageable. AdLC8 has been shown to efficiently function as a helper virus in the Cre/loxP helper-dependent system (Parks et al. 1996, *Proc. Natl. Acad. Sci.* in press). Likewise, a second helper virus AdLC8cluc (Parks et al. 1996, *Proc. Natl. Acad. Sci.* in press) similarly having deletions of E1 and E3 sequences but having a luciferase expression cassette in E3 can efficiently function as a helper virus. In the present invention, a new helper virus is constructed that contains a defective or deleted pIX coding region.

Figure 3B:
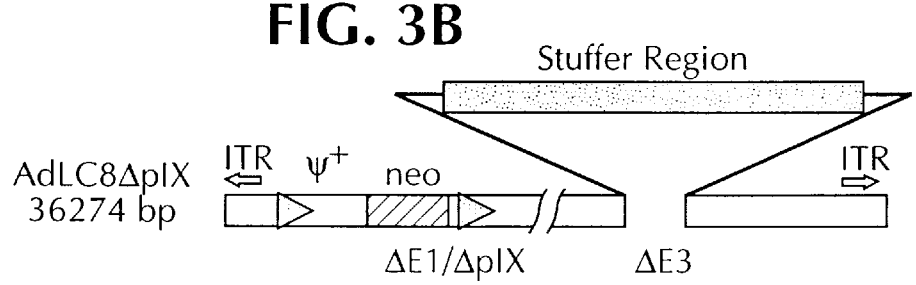

In this example, not meant to be limiting, the new helper virus, similar to AdLC8, incorporates an expanded E1 deletion that also removes the pIX coding sequences, which is designated in this example AdLC8ΔpIX (FIG. 3B). AdLC8ΔpIX includes a large stuffer sequence replacing the E3 region, which increases the size of the helper virus to ~36.3 kb. In the example, insertion of a stuffer sequence in E3 has two advantages. First, the large stuffer DNA will increase the genome of the virus well above the size limit for packaging in a pIX-defective capsid, thus preventing helper virus packaging in cells that do not complement the pIX deficiency. Secondly, recombination between the helper virus and Ad sequences contained in 293 and 293-derived cells generates viral DNA that exceeds the upper packaging limit for Ads, preventing the formation of replication competent adenoviruses (RCA).

Figure 4:
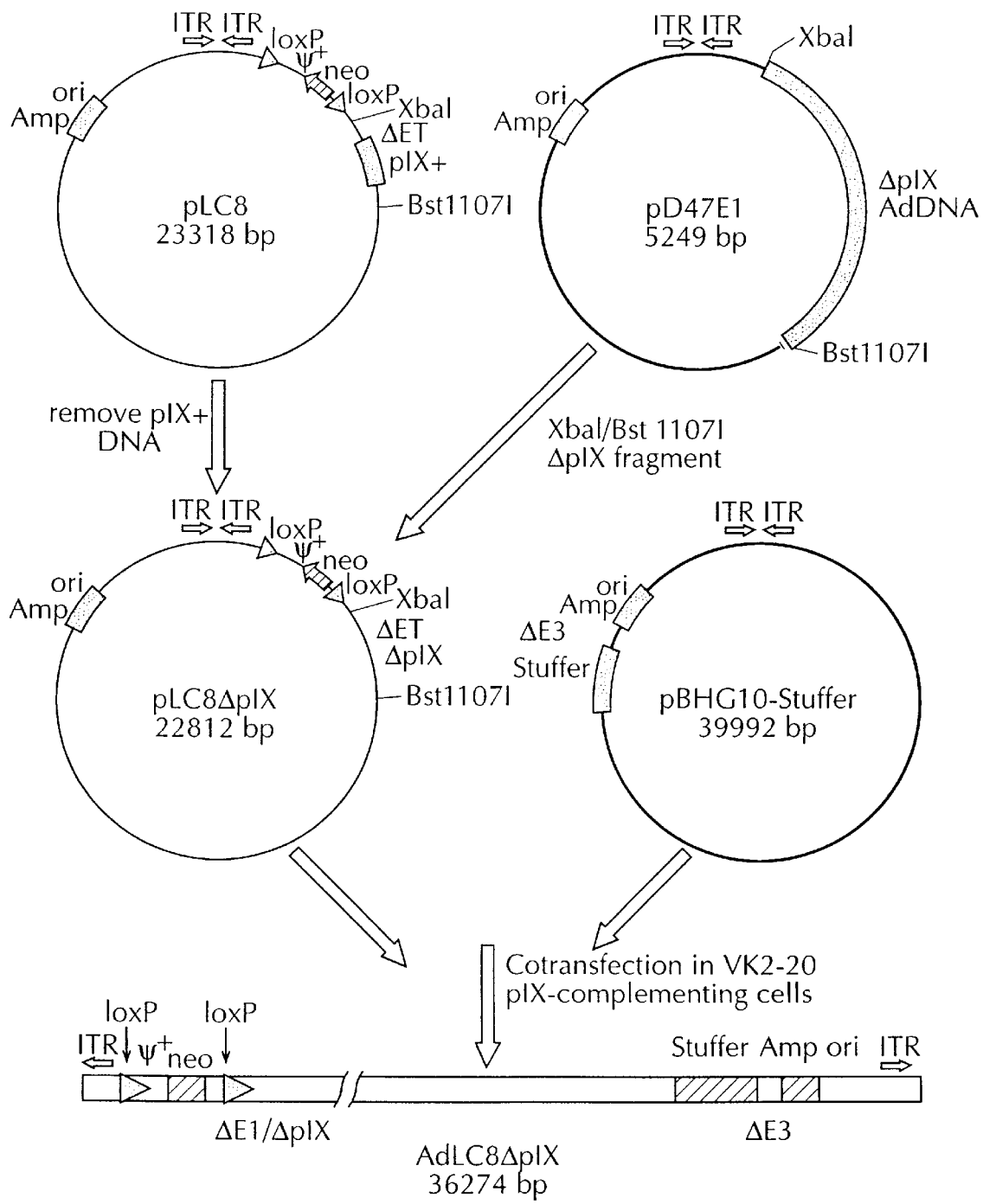
FIG. 4 is a diagrammatic representation of the construction of a helper virus lacking pIX and containing a loxP flanked packaging signal.
Figure 5:
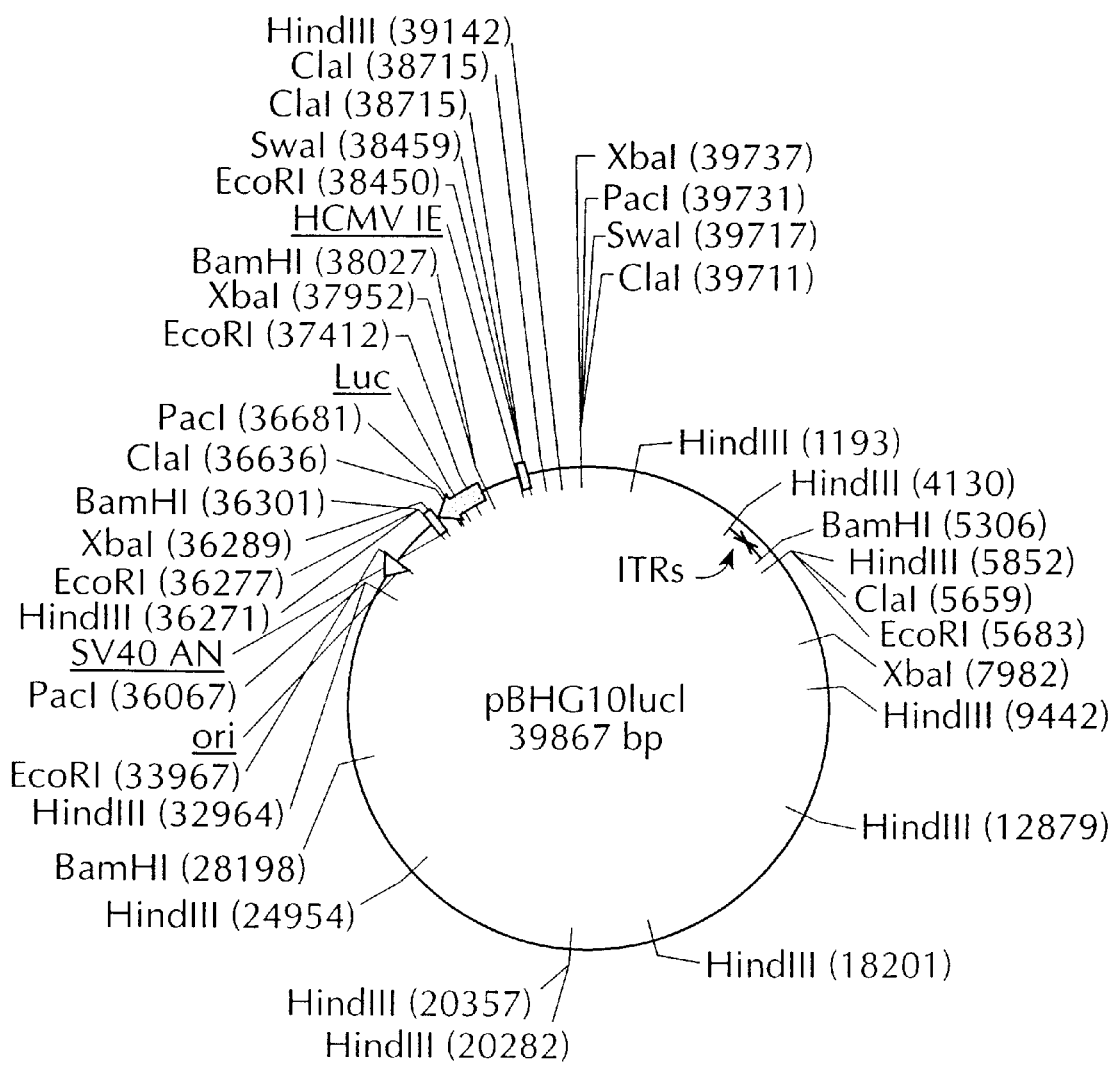
FIG. 5 is a diagrammatic representation of the structure of pBHG10luc1 derived plasmid containing an E3 stuffer sequence including a luciferase expression cassette.
Figure 6:
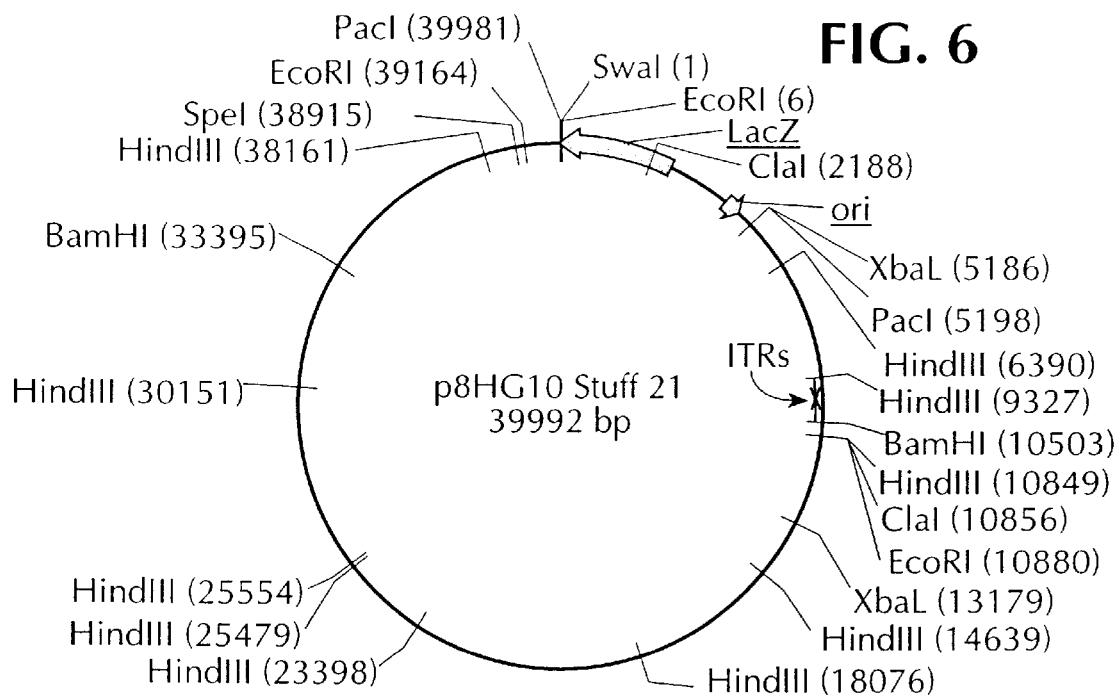
FIG. 6 is a diagrammatic representation of the structure of a pBHG10 derived plasmid pBHG10stuff21 containing an E3 stuffer sequence including a DNA segment derived from the LacZ gene and from plasmid pBR322.

In the example shown in FIG. 4, an XbaI/BstI 1071 fragment from pD47E1, a plasmid containing Ad sequences with the appropriate pIX deletion, is used to replace the equivalent region in pLC8, generating pLC8ΔpIX. This introduces a pIX deletion into a plasmid containing a loxP-flanked packaging signal and ITRs. When cotransfected into cells that complement both the E1 and pIX deficiencies, pLC8ΔpIX and a second vector pBHG10-stuffer will recombine and can be recovered as an Ad virus AdLC8ΔpIX. pBHG10-stuffer is a plasmid that contains the majority of the coding sequences of the Ad genome, with the exception of the E1 and E3 regions. Here, the E3 region of pBHG10 includes a stuffer sequence. Suitable stuffer sequences for use with the present invention are sequences derived from lambda phage DNA, portions of the *E. coli* lacZ gene, and sequences derived from a plasmid such as pBR322. These examples are suitable stuffer sequences and are not meant to be limiting, as sequences derived from numerous other organisms such as human, insect, viral or yeast DNA would be equally suitable. pBHG10-stuffer also lacks the viral packaging signal and therefore cannot itself be packaged into infections virions. Examples of other second vectors including stuffer sequences which are suitable for obtaining the helper viruses of the present invention include pBHG10luc1 (FIG. 5) and pBHG10stuff21(FIG. 6).

Once the helper adenovirus, AdLC8ΔpIX, is obtained it is then "rescued" and propagated in a pIX-complementing cell line, such as, VK2-20 or VK4-24 (Krougliak and Graham 1995, *Hum. Gene Ther.*, 6:1575–1586), using standard techniques.

Figure 8:
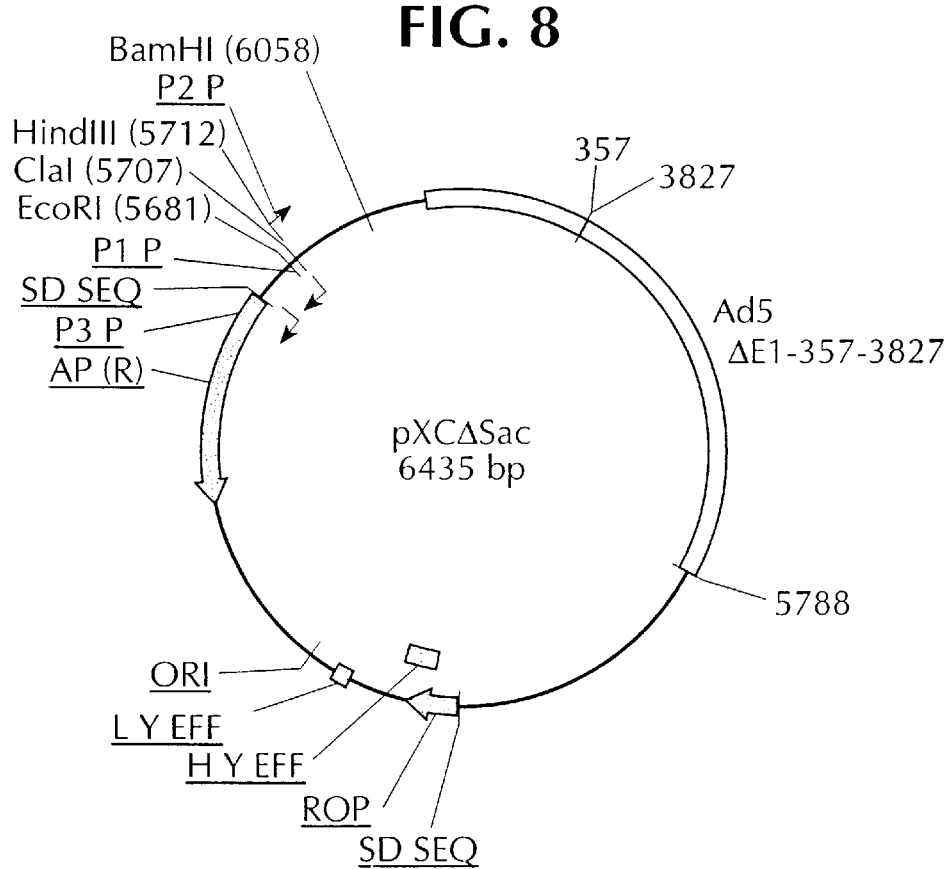
FIG. 8 is a diagrammatic representation of the structure of a plasmid pXCΔSac containing Ad sequences from the left end of the genome to nucleotide 5788 and having an E1 deletion extending into pIX.
Figure 7:
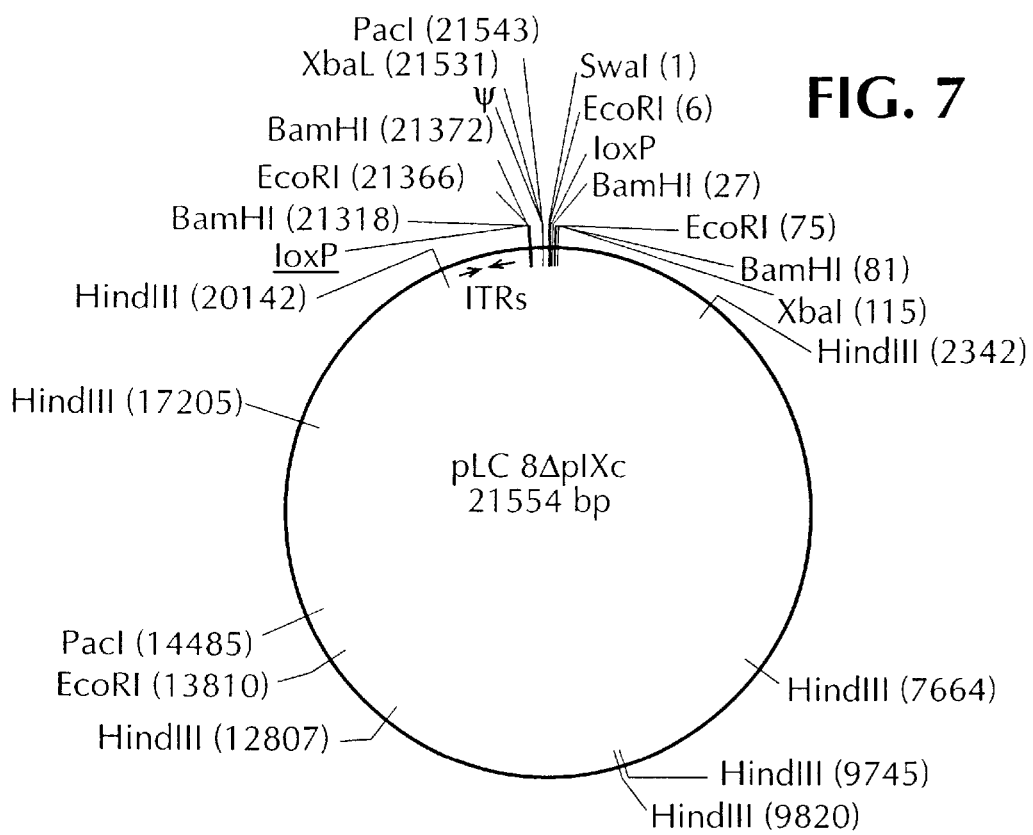
FIG. 7 is a diagrammatic representation of the structure of a plasmid pLC8Δp1Xc containing Ad sequences with loxP sites flanking the packaging signal (ψ) and having an E1 deletion extending into pIX.

VK2-20 and VK4-24 cell lines are derived from 293 cells and can also complement the E1 deletion in AdLC8cΔpIX. AdLC8cΔpIX, hereafter referred to as the helper virus, will be capable of producing all of the factors, with the exception of pIX, necessary for the replication and packaging of an Ad genome in cells that are permissive for the growth of E1-deleted viruses. In this and other examples, removal of the E1 or E3 regions or inclusion of the loxP-flanked packaging signal is not meant to be limiting since other deletions or no deletions may equally be engineered into the parent plasmid, and resulting helper virus, and be suitably employed in place of the example shown above. For example, other first vectors suitable for obtaining the helper virus of the present invention include, pLC8ΔpIXc (FIG. 7) derived from pLC8ΔpIX by removal of the neo coding sequence by digestion with restriction endonuclease Swa I and ligation of the vector, as well as pXCΔSac (FIG. 8).

Figure 9:
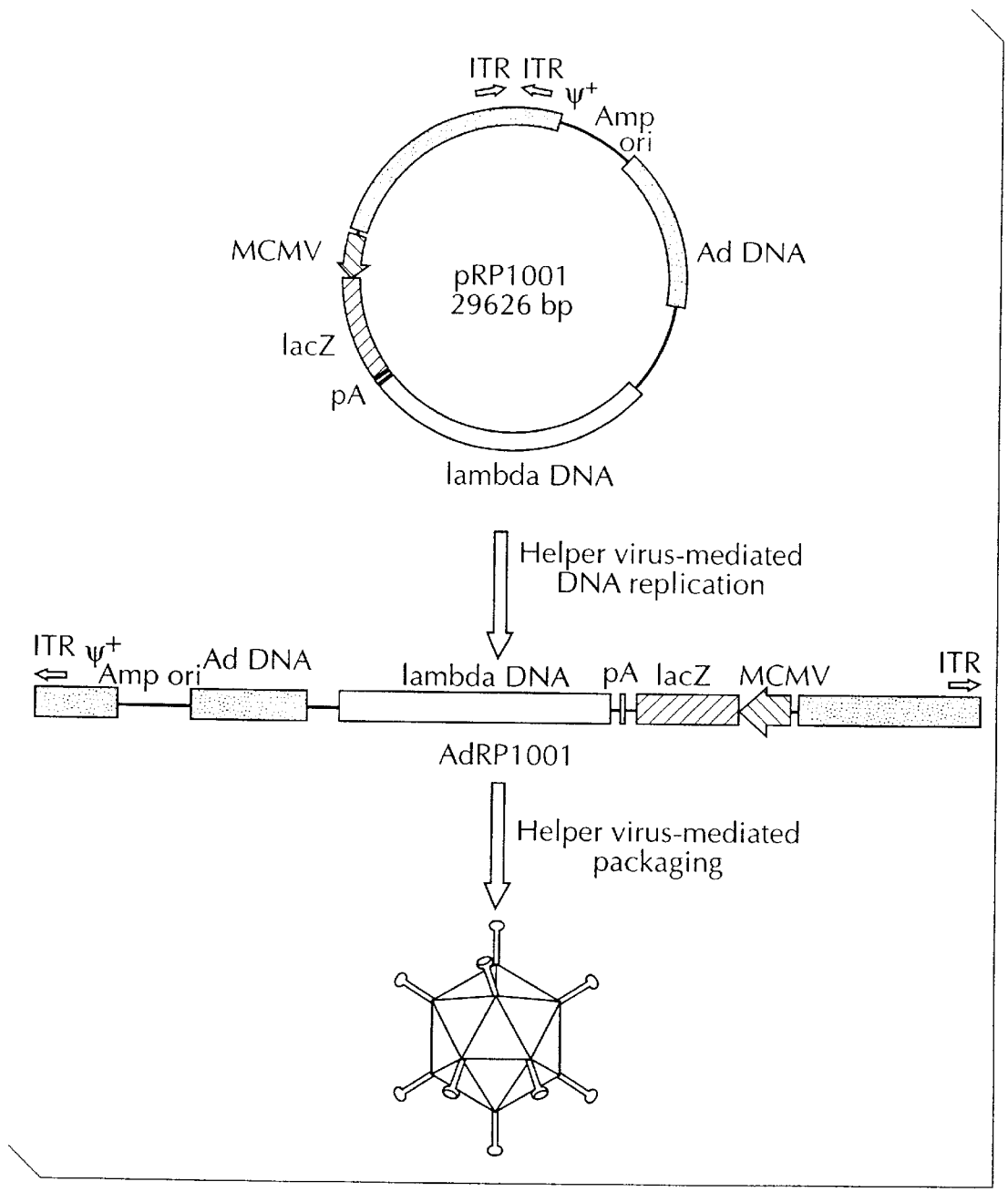
FIG. 9 is a diagrammatic representation of the helper-dependent vector.

The present invention provides for the development of helper-dependent vectors that lack substantial portions of the Ad genome, similar to those described in the Cre/loxP application. An example of the helper-dependent vector is shown in FIG. 9. Helper-dependent vector pRP1001 includes adenoviral DNA including the ITRs and packaging signal (ψ), a bacterial origin of replication (ori), an ampicillin resistance(Amp) gene, murine cytomegalovirus immediate early promoter (MCMV), a β-galactosidase gene (lacZ), polyadenylation signal (pA), and lambda DNA. pRP1001 and a suitable helper virus, such as, for example, AdLC8ΔpIX are connected into a suitable host cell to obtain packaged helper-dependent vector AdRP1001.

The genomes of the helper-dependent vectors need contain only those sequences required in cis for viral replication: the Ad ITRs and packaging signal, comprising approximately 500 bp of Ad DNA. Optionally, other viral sequences may be present, as well as stuffer sequences and other DNA segments encoding foreign genes and regulatory elements such as promoters, enhancers and polyadenylation signals.

The third embodiment of the invention provides a cell line that can support the replication of the viral components of the invention. Mammalian cell lines which express recombinases are suitable for use with the present invention. A mammalian cell line which expresses the Cre recombinase is preferred. A cell line expressing Cre recombinase can be connected with the helper virus and helper-dependent vector. One example of such a cell line, not meant to be limiting, is the 293Cre4 cell line which has been developed and characterized (Chen and Graham 1996, unpublished results). 293Cre4 cells were constructed by transfection with a plasmid containing an expression cassette consisting of the bacteriophage P1 Cre recombinase under the regulation of the human cytomegalovirus immediate early promoter and Simian virus 40 polyadenylation sequence, and a neomycin resistance cassette. Selection for neomycin resistant colonies led to the identification of several 293Cre cell lines which have been analyzed and shown to stably express the Cre recombinase. Upon infection of 293Cre cells, the packaging signal of AdLC8 is efficiently excised from approximately 90% of the helper virus DNA (Parks et al. 1996, *Proc. Natl. Acad. Sci* in press).

The fourth embodiment of the invention, a cell line that supports the replication of the viral components of the invention, that expresses the Ad pIX, and that can be transfected with plasmids described in the previous examples has also been developed. Preferably, the cell line is a human cell line; however, other cell lines are also suitable such as Syrian hamster, mouse, bovine, porcine, or canine cells. These examples are not meant to be limiting as cells derived from other species are also suitable for use with the present invention. A 531 bp fragment of Ad5 DNA containing the pIX gene was placed under the regulation of an inducible metallothionein promoter or under the control of the human cytomegalovirus immediate early gene promoter and the Simian virus 40 polyadenylation sequence, transfected into 293 cells, and several clones that stably express pIX were identified (Krougliak and Graham 1995, *Hum Gene Ther*. 6:1575–1586). Cell lines VK2-20, VK4-24 and VK10-9 are capable of complementing a pIX-deficient Ad, and viral titers are similar to that of wild-type virus.

Figure 10:
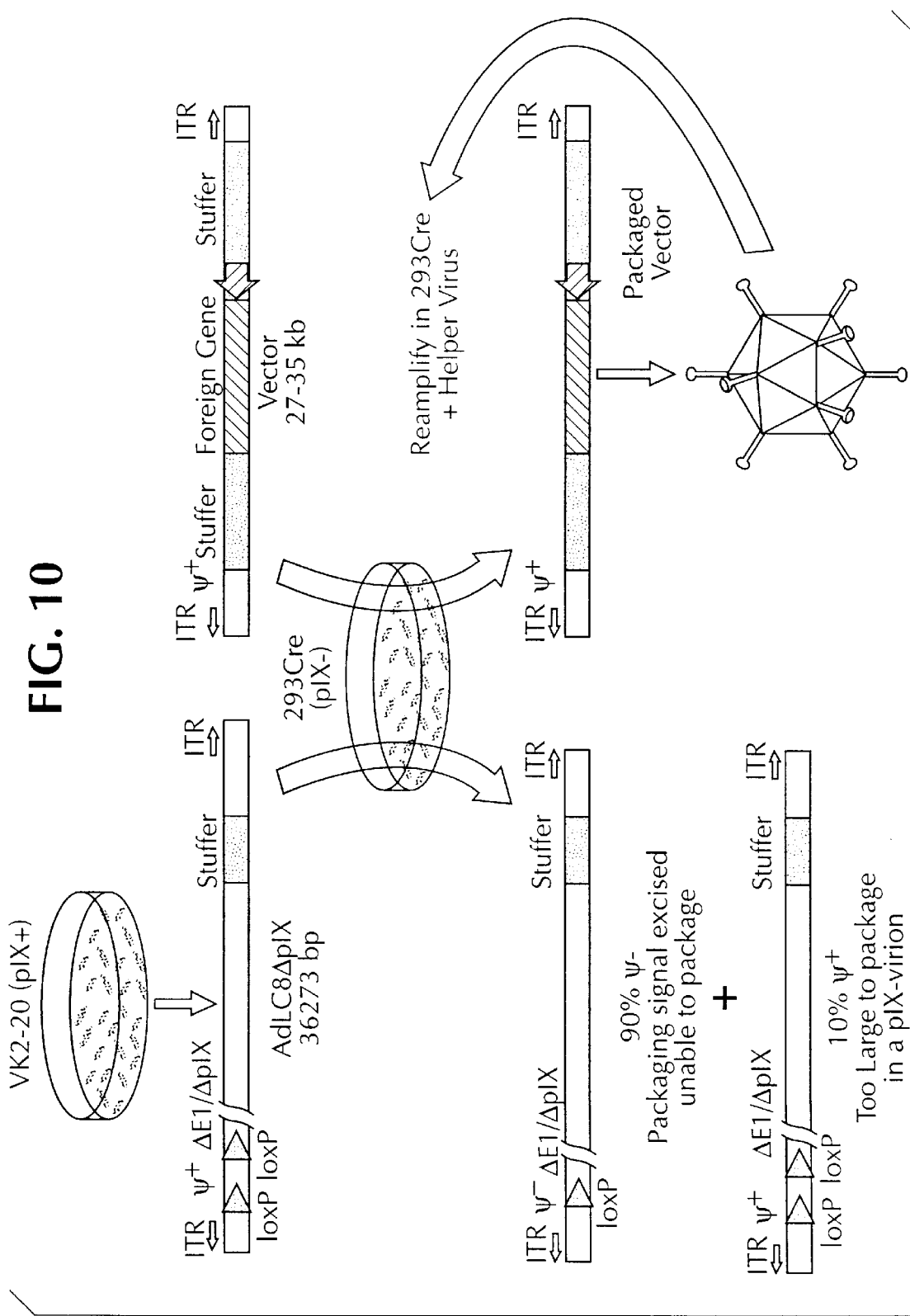
FIG. 10 is a diagrammatic representation of the Cre/loxP/ΔpIX helper-dependent system.

The titer of the helper-dependent vector can be increased by serial passage through helper virus-infected 293Cre cells. An example of the general strategy for amplification of helper-dependent vectors in AdLC8ΔpIX-infected cells is shown in FIG. 10. AdLC8ΔpIX is grown in VK2-20, a cell line that will complement the pIX-deficiency and allow the packaging of the helper virus DNA. Upon infection of the 293Cre, a cell line that will not complement the pIX deficiency, the viral packaging signal will be excised from AdLC8ΔpIX, rendering the virus unpackageable. Removal of the viral packaging signal ensures that packaging factors are not "diluted out" by binding to the helper virus DNA. Helper virus DNA that escapes the Cre-mediated excision of the packaging signal will be too large (i.e., greater than about 35 kb) to package in the pIX cell environment. However, both the recombined and unrecombined viral DNA can provide all of the functions necessary to package an Ad vector of the appropriate size (27 to 35 kb). In this manner, two separate mechanisms, Cre-mediated excision of the viral packaging signal and the DNA size constraints imposed on a pIX-defective virus are used to ensure the complete elimination of all helper virus from vector preparations. These two mechanisms could be used separately to enhance the packaging of the helper dependent vector DNA relative to helper virus DNA but when employed together will provide a greater degree of such enhancement.

Figure 12A:
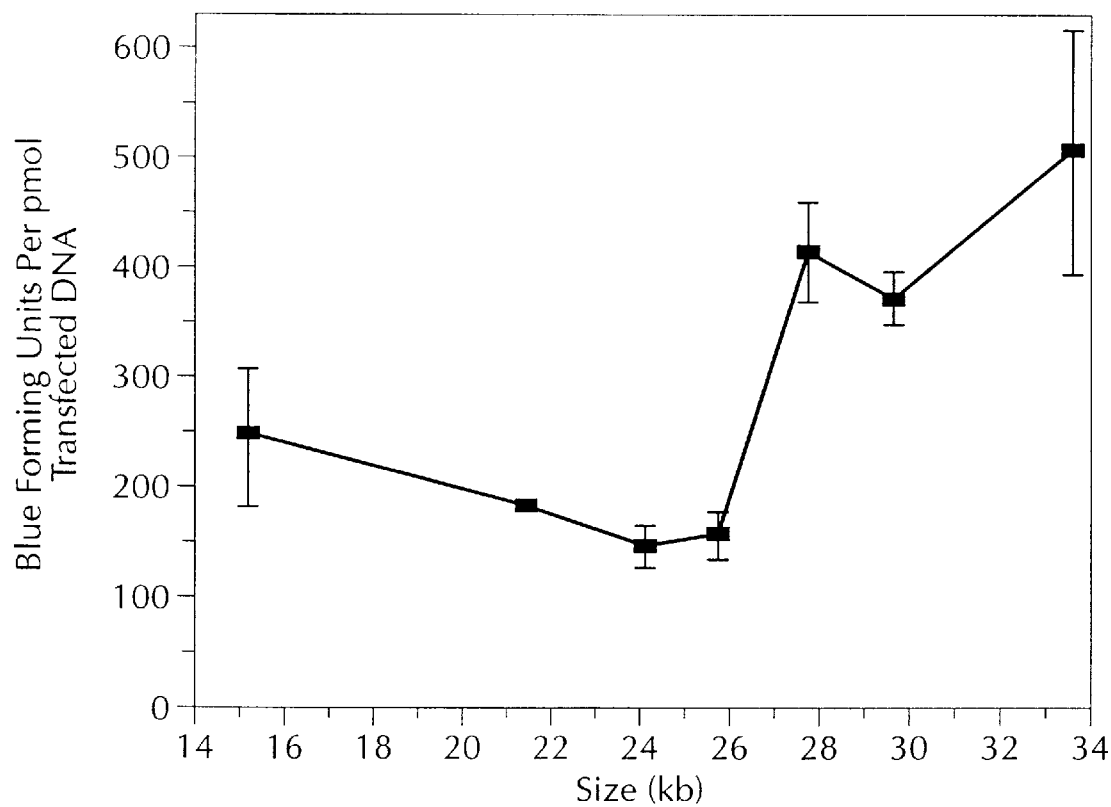
FIGS. 12A–12B is a graphical representation of amplification of helper-dependent vectors as a function of genome size.
Figure 12B:
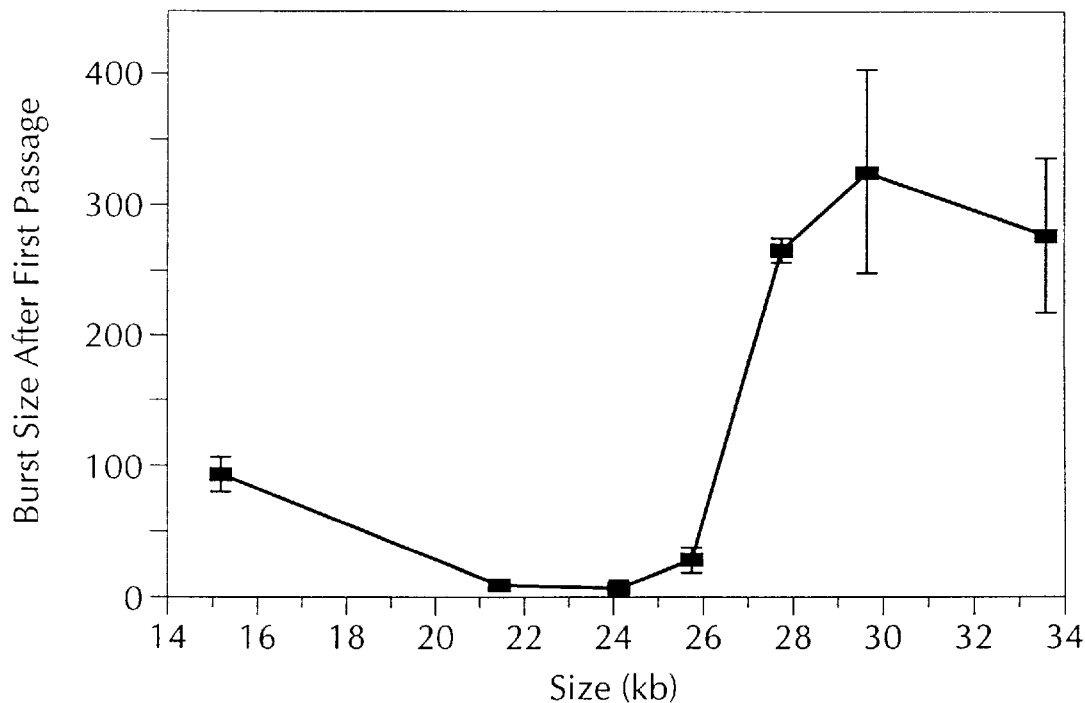

To examine the effect of helper-dependent vector DNA size on packaging efficiency, a series of plasmids were constructed ranging from 15.1 to 33.6 kb, containing ψ and the ITRs, as well as a β-galactosidase (lacZ) reporter gene under the control of the murine cytomegalovirus immediate-early promoter (MCMV) and Simian Virus 40 polyadenylation (pA) signal (FIG. 11). 293 cells were transfected with these plasmids and infected 18 hr later with a helper virus, AdLC8cluc (Parks et al. 1996), at a multiplicity of infection (MOI) of 5 PFU per cell. After complete CPE (~48 h post infection), the cells were scraped into the medium and freeze/thawed to release the virus. Aliquots (500 μl per 60 mm dish) of the crude viral lysates were used to infect 293 monolayers, and the monolayers were stained 20 h later to assay for the presence of β-galactosidase-expressing virus. No blue-staining cells were detected in cultures that were infected with control extracts prepared from transfection/ infections lacking either AdLC8cluc or vector DNA. Plasmids that were larger than 27 kb were efficiently converted into packageable linear molecules, as shown by the recovery of β-galactosidase-transducing particles (blue forming units, BFU) (FIG. 12). Vectors with genomes; less than 26 kb were recovered at a significantly reduced frequency compared to larger vectors, with an average recovery of less than half that of the larger vectors (175 versus 452 BFU per pmol of transfected DNA). This suggests that, during virion formation, DNA molecules that are smaller than ~75% of the wild type genome are packaged inefficiently. Curiously, AdRP1009, which is approximately half the size of the wild-type adenovirus genome, was packaged at a higher efficiency than the other small vectors which range in size from 21.3 to 25.7 kb.

Low recovery of BFU following calcium phosphate mediated transfection of vector DNA could be due to other factors besides inefficient packaging such as inefficient conversion to linear replicating DNA molecules. Therefore we examined the effect of vector length on packaging efficiency further by subjecting the viral lysates from the initial transfection to serial passage through AdLC8cluc-infected 293Cre4 cells. For the first passage, 293Cre4 cells were infected with 500 μl of vector-containing lysate. No additional helper virus was added since AdLC8cluc can replicate in the 293 cells used in the initial transfection, and was present in large quantities in the vector-containing lysate. After complete CPE, the infected cells were scraped into the medium, freeze/thawed, and again assayed for the presence of lacZ-encoding virus. After the first round of amplification, we examined the "burst" size for each virus. The input amount of virus was calculated based on the titer of the vector after the initial transfection. The output of virus was the total amount of vector obtained after the first amplification is in 293Cre4 cells and the burst size was calculated as the total viral yield divided by the virus input. Vectors with an overall size between ~21 and 26 kb yielded a burst size ranging from 10 to 30, whereas vectors greater than 27 kb had a burst size ranging from 270 to 330, or an average of about 17 times higher than that observed for the smaller vectors (FIG. 12). AdRP1009 (15.1 kb) continued to be more efficient than the other small vectors, and had a burst size of 95 or approximately 3–10 fold greater than that of the other vectors smaller than 27 kb.

Figure 13:
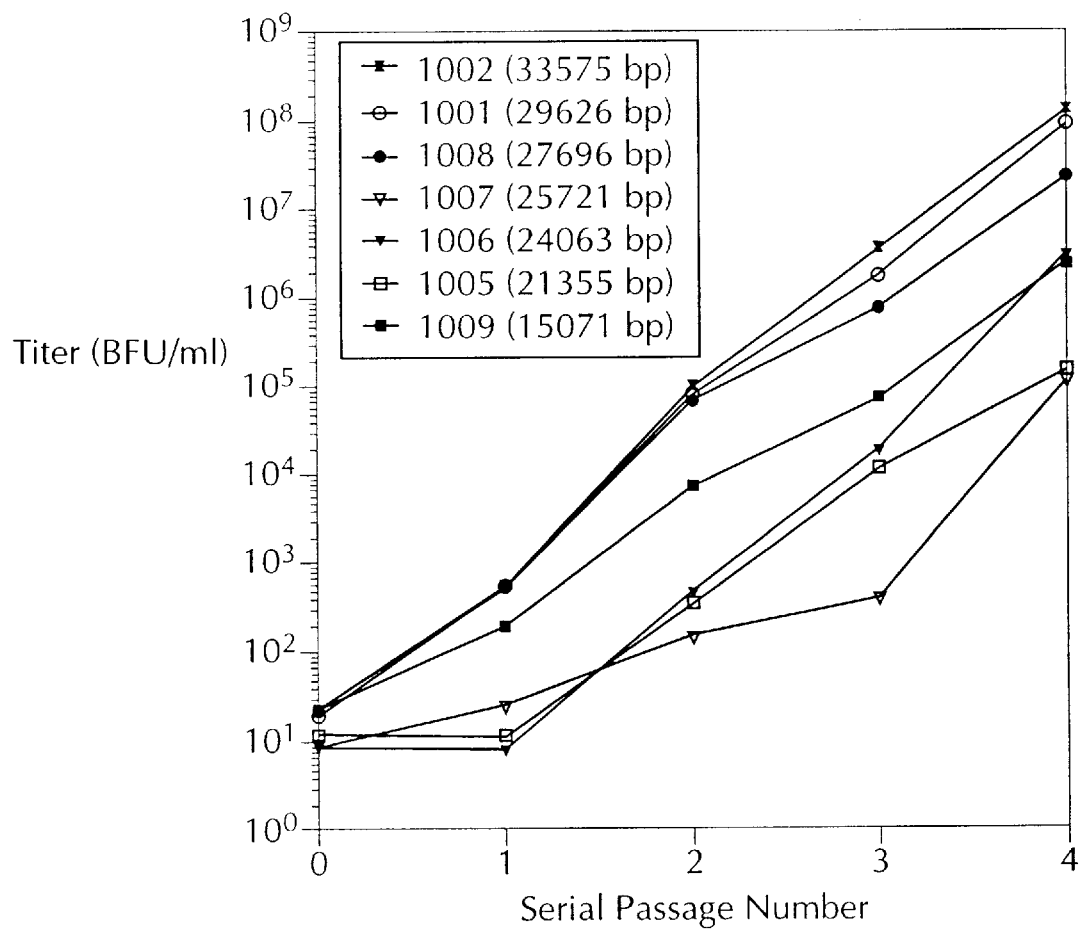
FIG. 13 is a graphical representation of amplification of helper-dependent vectors through serial passage in connected 293 Cre cells.

Vectors were subjected to further serial passage in AdLC8cluc-infected 293Cre4 cells, and the recovery of vector was examined. Similar quantities of each vector were used as inoculum for the first passage. Each amplification of AdRP1008, AdRP1001, and AdRP1002 (27.7 to 33.6 kb) resulted in a 10 to 100-fold increase in virus titer (FIG. 13) but recovery of vectors less than 26 kb was reduced over all passages. Vector DNA having less than ~75% of the wild type genome was replicated or packaged with a reduced efficiency and vectors greater than this were packaged with equal efficiency.

Our observation that a vector approximately half the size of the wild type Ad genome is replicated with a higher efficiency than other small vectors can be explained in two ways. It is possible that the packaged vector is a covalent dimer of the transfected plasmid, which would increase the size of the packaged vector to ~30 kb, a size which should be very efficiently packaged. Packaging of multimerized DNAs has been observed in Epstein-Barr virus (Bloss and Sugden 1994). Alternatively, the virion may contain two monomer copies of the vector, again increasing the size of the encapsulated DNA to 30 kb. The latter is not an unlikely possibility since packaging of multiple DNAs into a single phage head has recently been reported in P1 (Coren et al. 1995). Either of these mechanisms would result in the incorporation into the virion of two copies of a foreign gene encoded by the Ad vector.

Figure 14A:
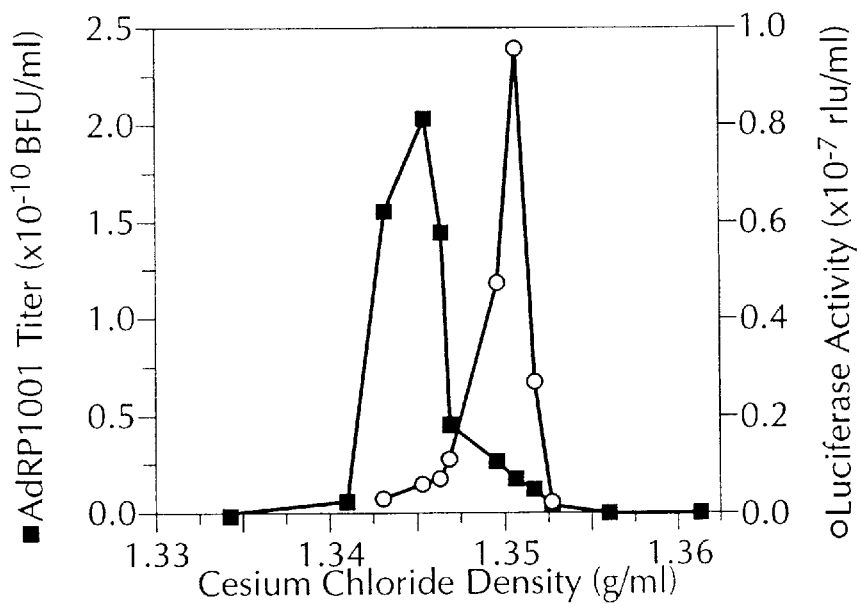
FIGS. 14A–C is a graphical representation of the results of fractionation of helper-dependent vectors AdRP1001 (29.7 kb), AdRP1005 (21.3 kb), and AdRP1009 (15 kb) in CsCl buoyant density gradients.
Figure 14B:
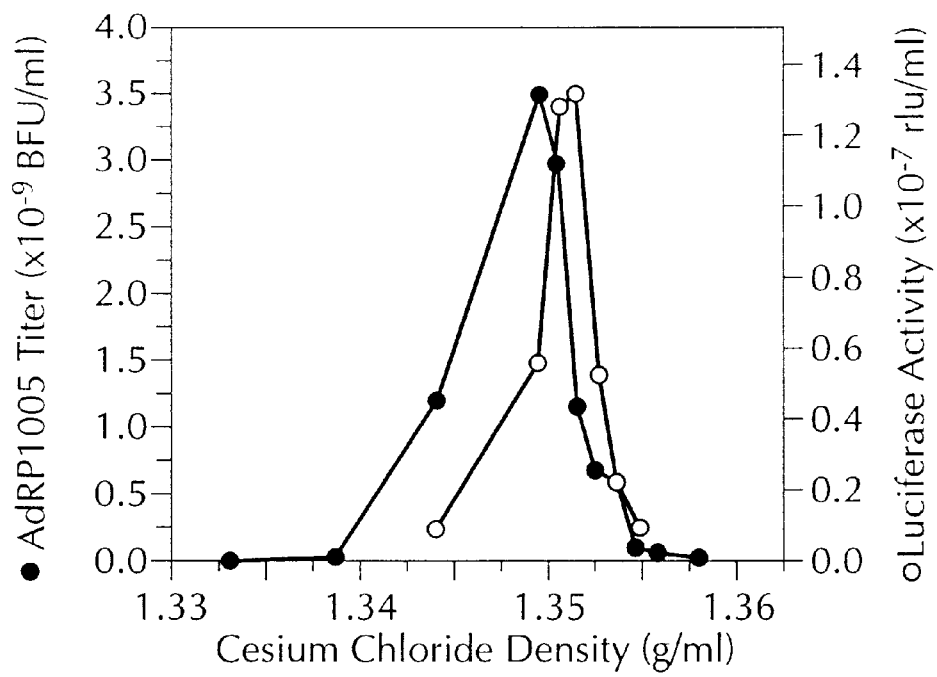
Figure 14C:
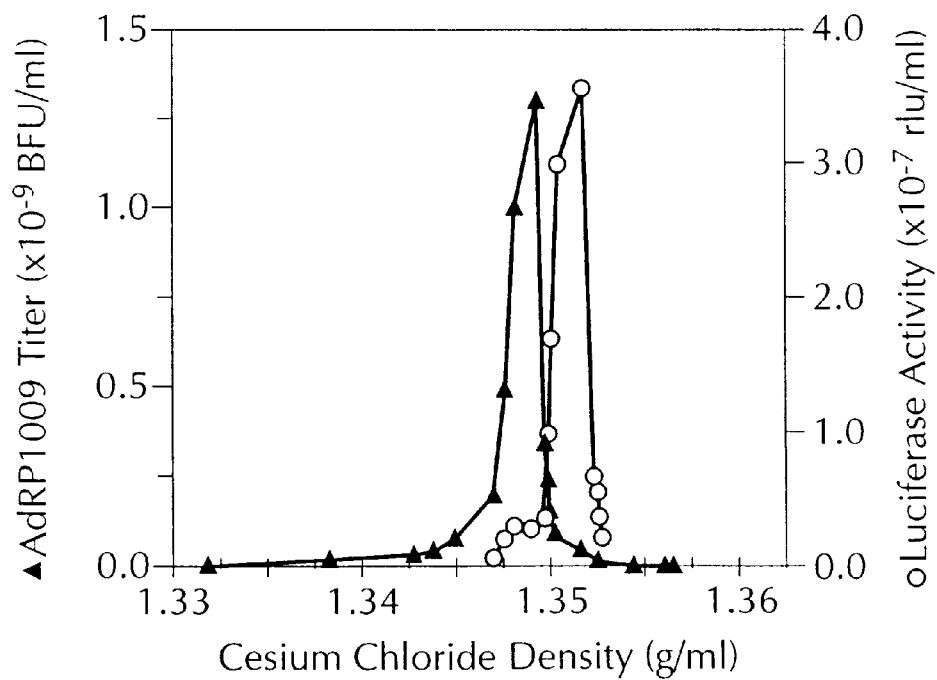

To distinguish between the two mechanisms, large scale preparations of AdRP1009 (15 kb), AdRP1005 (21.3 kb) and AdRP1001 (29.7 kb) were performed and the resulting vector fractionated on a CsCl density gradient. Fractions were collected through the viral bands and each of these fractions were assayed for the presence of blue-forming and luciferasetransducing particles (FIG. 14). Luciferase activity is expressed by the AdLC8cluc helper virus. AdRP1001 was partially separated from the helper virus due to the difference in density caused by the difference in DNA content between the vector (29.7 kb) and the helper virus AdLC8cluc (35.4 kb). Both AdRP1005 and AdRP1009 would be predicted to migrate at a higher density than AdRP1001 due to their lower DNA content; however, this was not observed. Both AdRP1005 and AdRP1009 migrated to a CsCl density between AdRP1001 and AdLC8cluc, suggesting that the AdRP1005 and AdRP1009 virions contained DNA of between 29.6 and 35.4 kb, and not 15 kb and 21.3 kb, respectively, as would be predicted based on the size of the original transfecting plasmid.

Figure 15:
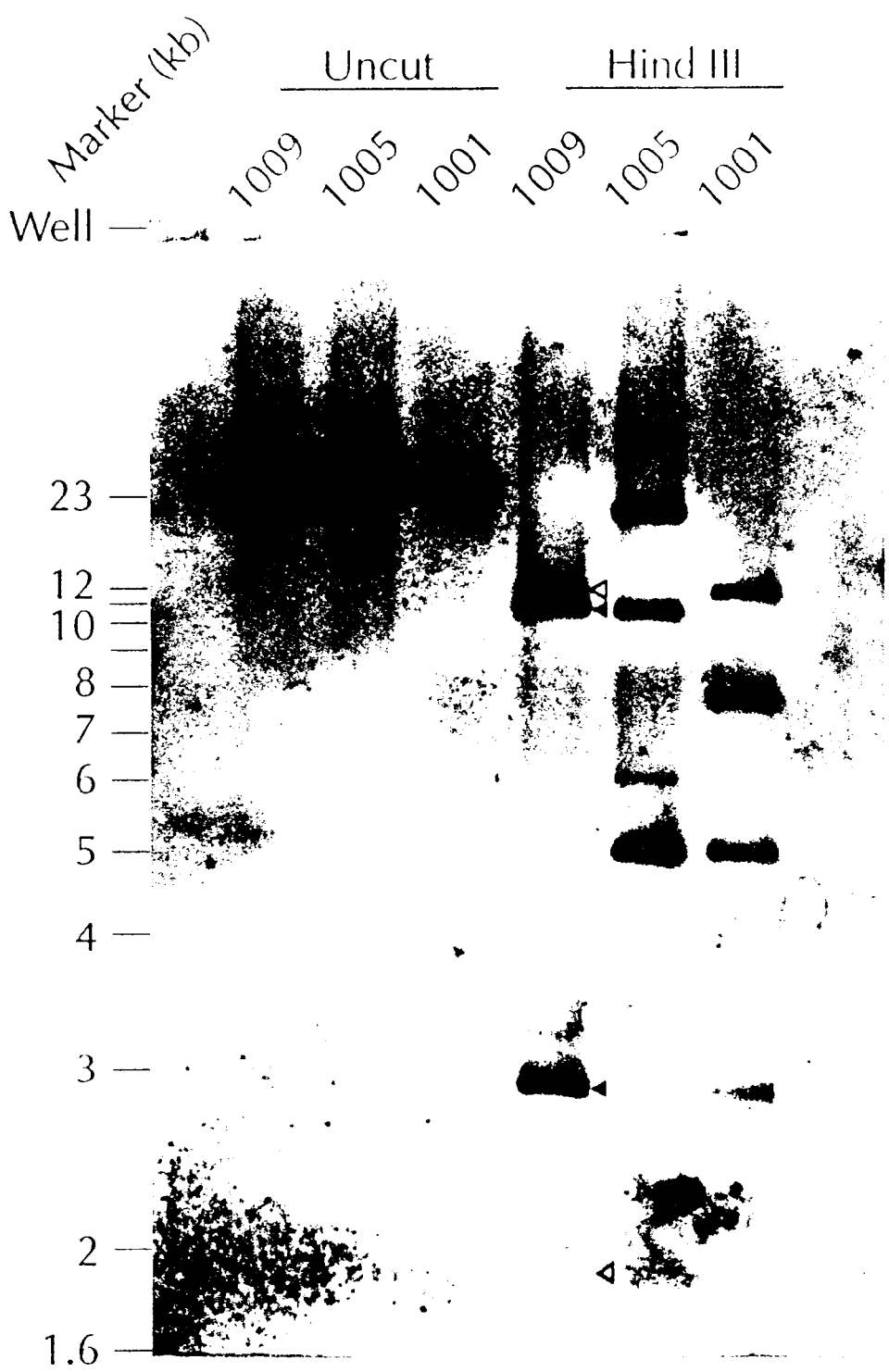
FIG. 15 is an autoradiograph showing Southern blot hybridization analysis of DNA from helper-dependent vectors AdRP1001, AdRP1005, and AdRP1009 after amplification in AdLC8cluc-infected 293Cre cells.

To analyze the structure of the DNA contained in the virions fractionated in FIG. 14, DNA was extracted and purified from the peak fractions of BFU for each vector, and analyzed by restriction digestion and Southern blot hybridization (FIG. 15). Uncut vector DNA was also analyzed and revealed that neither AdRP1009 (15 kb) nor AdRP1005 (21.3 kb) were of the predicted size based on the transfecting plasmid. Both of these vectors had an apparent size of greater than 23 kb. A minor band of approximately 15 kb was also observed in the lane containing uncut DNA from AdRP1009, and this may represent the packaging of two noncovalently-joined monomer molecules of AdRP1009 or small amounts of contamination of virions containing only a single copy of the monomer AdRP1009 genome. Analysis of vector DNA restricted with HindIII showed that the restriction pattern obtained for AdRP1009 (original size of 15 kb, with a predicted HindIII restriction pattern of 11.1, 2.9, and 1.0 kb, and indicated by black arrows in FIG. 15) was consistent with a structure in which the virion DNA had formed covalently joined head-to-tail and tail-to-tail concatemers, creating diagnostic restriction fragments of 12.1 and 1.8 kb, respectively, as indicated in FIG. 15 by white arrows. The 1.0 kb HindIII restriction fragment of AdRP1009 is not visible in FIG. 15, but was visible on overexposure of the film to the hybridized blot. Thus, starting with vector DNA which is approximately one half of the size required for efficient packaging in virions, successive passages of virus results in a selection for viral DNA that has formed concatemers. Vector DNA of ⅓ or ¼ or ⅕, etc., the optimum size for packaging would therefore tend to form covalently joined trimeric, tetrameric, or pentameric species. Viral DNA from AdRP1005 (originally 21.3 kb in size), with a predicted HindIII restriction pattern of 12.4, 5.1, 2.9, and 1.0 kb generated a vector that had rearranged to a more complex structure(s), with an overall size of greater than 30 kb. As expected, the restriction pattern for AdRP1001, with vector DNA that is above the lower cutoff for Ad packaging efficiency, was identical in structure to that predicted from the original transfecting plasmid, and had therefore not undergone rearrangement. Use of vector DNA that is of a size able to form covalently joined concatemeric species is advantageous for the development of vectors to be used in gene therapy since less virus is required to attain the same level of expression of the foreign protein, due to the presence of multiple copies of the gene. Similarly, vectors could be constructed that contain two or more tandem copies of a foreign gene, and this arrangement might be stably maintained if the vector size was only slightly higher than the packaging limit of 27 kb. Vector DNA that had undergone rearrangements to remove one copy of the foreign gene would be packaged with a lower efficiency and would be selected against. The clear demonstration of a lower packaging limit for adenoviruses will permit the design of vectors that are more stable and may lead to the development of vectors that express multiple copies of the foreign gene, requiring lower virus loads to attain the same level of expression as existing Ad vectors.

The foregoing examples are not meant to be limiting. It will be understood that various modifications may be made to the embodiments disclosed herein. A person skilled in the art may equally construct a helper virus whose genome is too large to be packaged into a pIX virion but which contains alternate insertions and or deletions. Other sequences could be inserted in E3, the E3 sequences of the virus could be retained, insertions could be introduced into other positions in the viral genome to produce a helper virus having a genome of appropriate size. Similarly, a person skilled in the art could construct other forms of vector that could be replicated in the presence of a suitable helper virus. Therefore, the above description should not be construed as limiting, but merely an exemplification of preferred embodiments. Those skilled in the art will envision other modifications within the scope of the claims appended hereto.

We claim:

1. A method for producing packaged, high-cloning capacity adenovirus virions which comprises:

(a) introducing into a mammalian host cell which does not encode or contain active wild-type pIX protein, such that said cell is permissive for packaging of a helper-dependent adenovirus vector into and replication and production of said adenovirus virions, but non-permissive for packaging of DNA of a helper adenovirus:

(i) a packaging-defective helper adenovirus comprising: a genome size greater than about 35 kb, sufficient adenovirus DNA to allow replication of a helper-dependent adenovirus vector, and a deletion or mutation of adenovirus DNA encoding pIX, wherein the DNA of said helper adenovirus is incapable of being packaged in the absence of wild type pIX protein, and (ii) a helper-dependent adenovirus vector incapable of viral replication in the absence of virion proteins encoded by said helper virus, wherein said vector comprises: a genome size less than about 35 kb, an adenoviral left ITR, an adenoviral right ITR, an adenoviral cis-acting packaging signal, no active or wild-type pIX encoding sequences, and at least one foreign DNA insert, and further wherein said vector is capable of being packaged into said virions under conditions in which the DNA of said helper adenovirus is not packaged; and (b) recovering said virions;

wherein said packaging signal in said helper adenovirus is flanked by loxP sites recognizable by Cre recombinase.

2. The method according to claim 1 wherein said vector further comprises a deletion of up to about 35,500 bp of adenovirus genomic DNA in order to generate said helper-dependent adenovirus vector comprising a genome size less than about 35 kb, while accommodating said adenoviral left ITR, said adenoviral right ITR, said adenoviral cis-acting packaging signal, and said at least one foreign DNA insert.

3. The method according to claim 1 wherein said host cell expresses Cre recombinase capable of catalyzing site-specific recombination between said loxP sites.

4. The method according to claim 1, wherein said vector has a genome size between about 27 kb and about 35 kb and between about 13 kb and about 18 kb.

5. The method according to claim 1 wherein said vector has a genome size between about 27 kb and about 35 kb and comprises at least two copies of a repeated foreign DNA.

6. The method of claim 4 wherein said packaged, high cloning-capacity virions comprise a concatemer of said vector having a genome size from about 13 kb to about 18 kb, wherein said concatemer has a genome size of from about 27 to about 35 kb.

7. A packaged, high cloning-capacity helper-dependent adenovirus vector produced by the method of claim 1.

8. A method for producing a helper adenovirus which comprises:

(a) co-transfecting a mammalian host cell permissive for replication and packaging of the DNA of said helper adenovirus under conditions allowing production of said helper adenovirus with:

(i) a first plasmid comprising adenovirus DNA having a deletion or mutation of adenovirus DNA encoding pIX, and having adenoviral packaging sequences flanked by recombinase recognition sites, and sufficient adenovirus DNA to recombine with a second plasmid, and (ii) said second plasmid comprising adenovirus DNA having a bacterial origin of replication and an antibiotic resistance gene inserted into a non-essential region of said DNA, without sequences encoding adenoviral packaging sequences, and sufficient adenovirus DNA to recombine with said first plasmid, wherein recombination of said first and said second plasmids produces a helper adenovirus comprising a genome size greater than about 35 kb, adenoviral packaging sequences flanked by Cre recombinase recognition sites, sufficient adenovirus DNA to allow replication of a helper-dependent adenovirus vector and said deletion or mutation of adenovirus DNA encoding pIX such that in the absence of active or wild-type adenoviral pIX, the genome of said helper virus is inefficiently packaged; and (b) recovering said helper adenovirus in said cell wherein active or wild-type pIX is expressed, and wherein said Cre recombinase is not expressed.

9. The method according to claim 8 wherein the second plasmid comprises stuffer nucleic acid inserted into the E3 region of said adenovirus DNA.

10. The method of claim 8 wherein said second plasmid fluther comprises a deleted or mutated packaging signal.

11. A helper adenovirus comprising a genomic size greater than about 35 kb, a deletion or mutation of adenovirus DNA encoding pIX, and an adenovirus E3 region having stuffer nucleic acid inserted therein, wherein said helper adenovirus further comprises a packaging signal flanked by loxP sites recognizable by Cre recombinase and wherein no active or wild-type pIX protein is produced.

12. A kit for producing packaged, high-cloning capacity adenovirus virions comprising:

(a) a first mammalian host cell which stably expresses adenovirus pIX protein and adenovirus E1 protein;

(b) a packaging-defective helper adenovirus which comprises a genome size greater than about 35 kb, sufficient adenovirus DNA to allow replication of a helper-dependent adenovirus vector, and a deletion or a mutation of adenovirus DNA encoding pIX, wherein the DNA of said helper adenovirus is incapable of being packaged in the absence of wild type pIX protein;

(c) a helper-dependent adenovirus vector incapable of viral replication in the absence of said helper virus, wherein said vector comprises a genome size less than about 35 kb, an adenoviral left ITR, adenoviral right ITR, an adenoviral cis-acting packaging signal, no active or wild-type pIX encoding sequences, and at least one foreign DNA insert, and further wherein said vector is capable of being packaged into said virions under conditions in which the DNA of said helper adenovirus is not packaged, into a mammalian host cell permissive for replication and packaging of said vector into said virions but non-permissive for packaging of the DNA of said helper adenovirus; and (d) a second mammalian host cell permissive for replication and packaging of said vector into said virions but non-permissive for packaging of the DNA of said helper adenovirus, wherein said host cell does not express active or wild-type pIX protein;

wherein said helper adenovirus comprises a modified early region 1 (E1) having a packaging signal flanked by excision sites recognizable by a recombinase, wherein said recombinase is Cre recombinase and said excision sites are loxP sites.

13. The kit according to claim 12, wherein said second host cell stably expresses Cre recombinase.

14. A helper-delendent adenovirus vector system for producing packaged high cloning-capacity adenovirus virions comprising:

(i) a packaging-defective, helper adenovirus which comprises a genome size greater than about 35 kb, a modified E1 region having a packaging signal flanked by excision sites recognizable by a recombinase, sufficient adenovirus DNA to allow replication of a helper-dependent adenovirus vector, and a deletion or mutation of adenovirus DNA encoding pIX, wherein the DNA of said helper adenovirus is incapable of being packaged in the absence of wild type pIX protein; and (ii) a helper-dependent adenovirus vector incapable of viral replication in the absence of virion proteins encoded by said helper virus, wherein said vector comprises a genome size less than about 35 kb, an adenoviral left ITR, an adenoviral right ITR, an adenoviral cis-acting packaging signal, no active or wild-type pIX encoding sequences, and at least one foreign DNA insert, and further wherein said vector is capable of being packaged into said virions under conditions in which the DNA of said helper adenovirus is not packaged, wherein said packaging signal of said helper virus DNA is flanked by loxP sites recognizable by Cre recombinase.

15. The system according to claim 14, further comprising a host cell expressing Cre recombinase capable of catalyzing site-specific recombination between loxP sites present in said genome of said helper adenovirus.

16. The system of claim 14, wherein said vector further comprises a deletion of up to about 35,500 bp of adenovirus genomic DNA, in order to generate said helper-dependent adenovirus vector comprising a genome size less than about 35 kb, while accommodating said adenoviral left ITR, said adenoviral right ITR, said adenoviral cis-acting packaging signal, and said at least one foreign DNA insert.

17. The system of claim 14, wherein said vector has a genome size between about 27 kb and about 35 kb or between about 13 kb and about 18 kb.

18. The system of claim 17, wherein said packaged, high cloning-capacity virions comprise a concatemer of said vector having a genome size from about 13 kb to about 18 kb, wherein said concatemer has a genome size of from about 27 to about 35 kb.

19. The system of claim 14, wherein said vector has a genome size between about 27 kb and about 35 kb and comprises at least two copies of a repeated foreign DNA insert.

20. The system of claim 14, wherein said helper adenovirus comprises a genomic size greater than about 35 kb, a deletion or mutation of adenovirus DNA encoding pIX, and an adenovirus E3 region having stuffer nucleic acid inserted therein.

21. A helper-dependent adenovirus vector system for producing packaged high cloning-capacity adenovirus virions comprising:

(i) a packaging-defective, helper adenovirus which comprises a genome size greater than about 35 kb, sufficient adenovirus DNA to allow replication of a helper-dependent adenovirus vector, and a deletion or mutation of adenovirus DNA encoding pIX, wherein the DNA of said helper adenovirus is incapable of being packaged in the absence of wild type pIX protein; and (ii) a helper-dependent adenovirus vector incapable of viral replication in the absence of virion proteins encoded by said helper virus, wherein said vector comprises a genome size less than about 35 kb, an adenoviral left ITR, an adenoviral right ITR, an adenoviral cis-acting packaging signal, no active or wild-type pIX encoding sequences, and at least one foreign DNA insert, and further wherein said vector is capable of being packaged into said virions under conditions in which the DNA of said helper adenovirus is not packaged, wherein said helper adenovirus comprises a genomic size greater than about 35 kb, a deletion or mutation of adenovirus DNA encoding pIX, and an adenovirus E3 region having stuffer nucleic acid inserted therein, wherein said helper adenovirus further comprises a packaging signal flanked by loxP sites recognizable by Cre recombinase.

* * * * *